United States Patent
Chan et al.

(10) Patent No.: US 12,116,595 B2
(45) Date of Patent: Oct. 15, 2024

(54) TARGET-PRIMED MACROPHAGES AND THERAPEUTIC USES THEREOF

(71) Applicant: The Lundquist Institute for Biomedical Innovation at Harbor-UCLA Medical Center, Torrance, CA (US)

(72) Inventors: Liana Chan, San Pedro, CA (US); Scott G. Filler, San Pedro, CA (US); Michael R. Yeaman, Redondo Beach, CA (US)

(73) Assignee: The Lundquist Institute for Biomedical Innovation at Harbor-UCLA Medical Center, Torrance, CA (US)

( * ) Notice: Subject to any disclaimer, the term of this patent is extended or adjusted under 35 U.S.C. 154(b) by 415 days.

(21) Appl. No.: 17/277,197

(22) PCT Filed: Sep. 17, 2019

(86) PCT No.: PCT/US2019/051564
§ 371 (c)(1),
(2) Date: Mar. 17, 2021

(87) PCT Pub. No.: WO2020/061084
PCT Pub. Date: Mar. 26, 2020

(65) Prior Publication Data
US 2022/0033777 A1    Feb. 3, 2022

Related U.S. Application Data

(60) Provisional application No. 62/732,566, filed on Sep. 17, 2018.

(51) Int. Cl.
| | |
|---|---|
| C12N 1/20 | (2006.01) |
| A61K 35/74 | (2015.01) |
| A61P 31/04 | (2006.01) |
| C12N 5/0786 | (2010.01) |
| C12R 1/445 | (2006.01) |

(52) U.S. Cl.
CPC ............ C12N 5/0645 (2013.01); A61K 35/74 (2013.01); A61P 31/04 (2018.01); C12N 1/20 (2013.01); C12N 2500/72 (2013.01); C12R 2001/445 (2021.05)

(58) Field of Classification Search
None
See application file for complete search history.

(56) References Cited

U.S. PATENT DOCUMENTS

2009/0023596 A1    1/2009   Kolattukudy et al.

FOREIGN PATENT DOCUMENTS

| CN | 106267174 A | 1/2017 |
| WO | 2011085071 A2 | 7/2011 |

OTHER PUBLICATIONS

Garaude et al. Nature Immunology. 17, 1037-1045 (2016).*
Hanke et al. J. Immunol. Mar. 1, 2013; 190(5):2159-2168.*
Zaitseva et al. Infection and Immunity, Jun. 2001, vol. 69, No. 6, p. 3817-3826.*
Chavez-Galan et al. Journal of Immunology Research, vol. 2016, Article ID 408235, 17 pages.*
Gracey et al. PloS One, Aug. 2013, vol. 8, Issue 8, e69421, 10 pages.*
Sharma et al. The Journal of Infectious Diseases 2004; 190:107-14.*
Kubica et al. PloS One 3(1): e1409, Jan. 2008, 16 pages.*
International Search Report and Written Opinion for PCT/US2019/051564 dated Nov. 19, 2019, 9 pages.
Jablonski et al., "Novel Markers to Delineate Murine M1 and M2 Macrophages", PLoS One, 10(12): e0145342, pp. 1-25, 2015.

* cited by examiner

*Primary Examiner* — Oluwatosin A Ogunbiyi
(74) *Attorney, Agent, or Firm* — Sheppard Mullin Richter & Hampton LLP

(57) ABSTRACT

Cell populations, compositions, and methods are provided relating to target priming of macrophage cells. The macrophages, once primed or activated with a microorganism, can be used to prevent or treat infection by the microorganism. Likewise, once primed or activated by a tumor cell or tumor antigen, the macrophage cell can be used to prevent or treat tumor of the same kind. The priming can be carried out in vitro or ex vivo. The macrophages can be isolated from the subject of disease prevention or treatment.

11 Claims, 13 Drawing Sheets

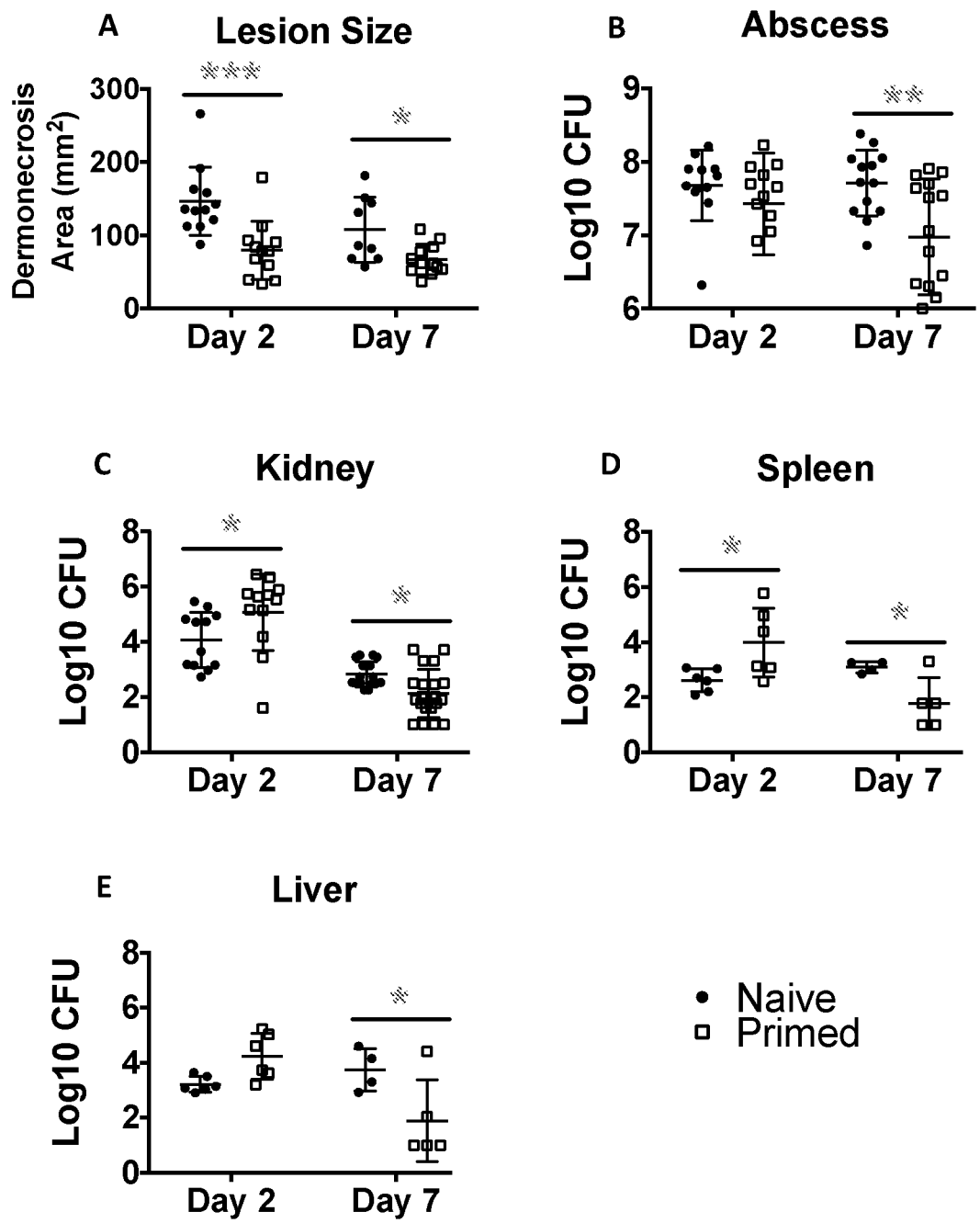
FIG. 1A-E

• Naive    □ Primed

• Naive    □ Primed

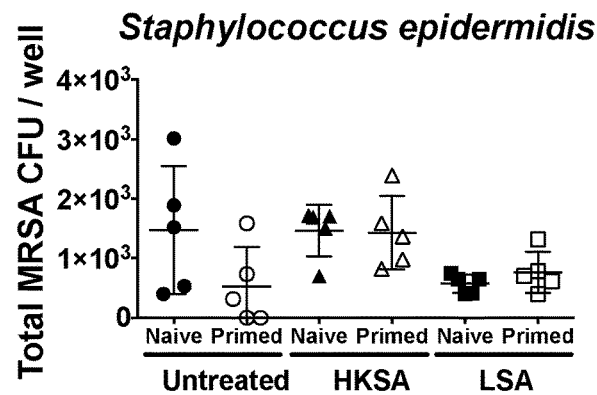
FIG. 5C
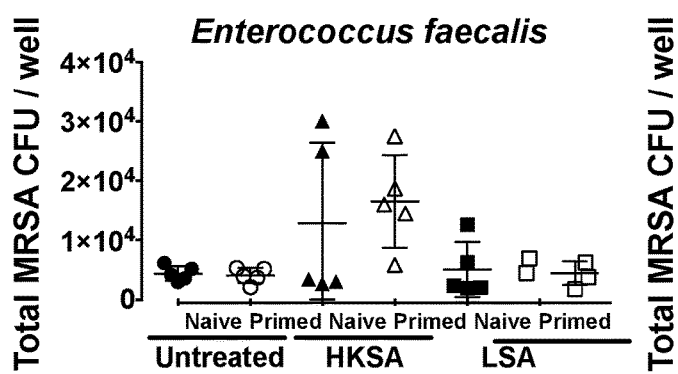 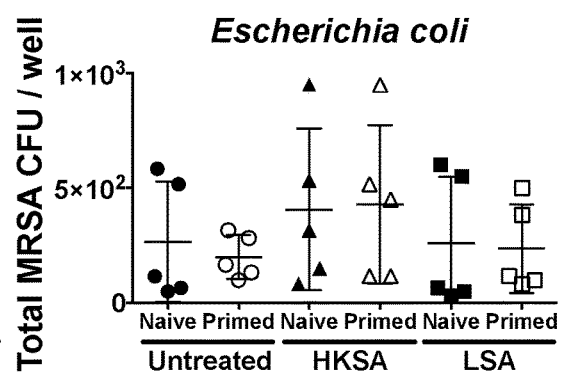
FIG. 5D
FIG. 5E

● No Mf   ■ Unt Naive BMDM   ▲ HKSA Naive BMDM   ◆ LSA Naive BMDM
⊖ No Mf   ⊟ Unt Primed BMDM  △ HKSA Primed BMDM  ◇ LSA Primed BMDM

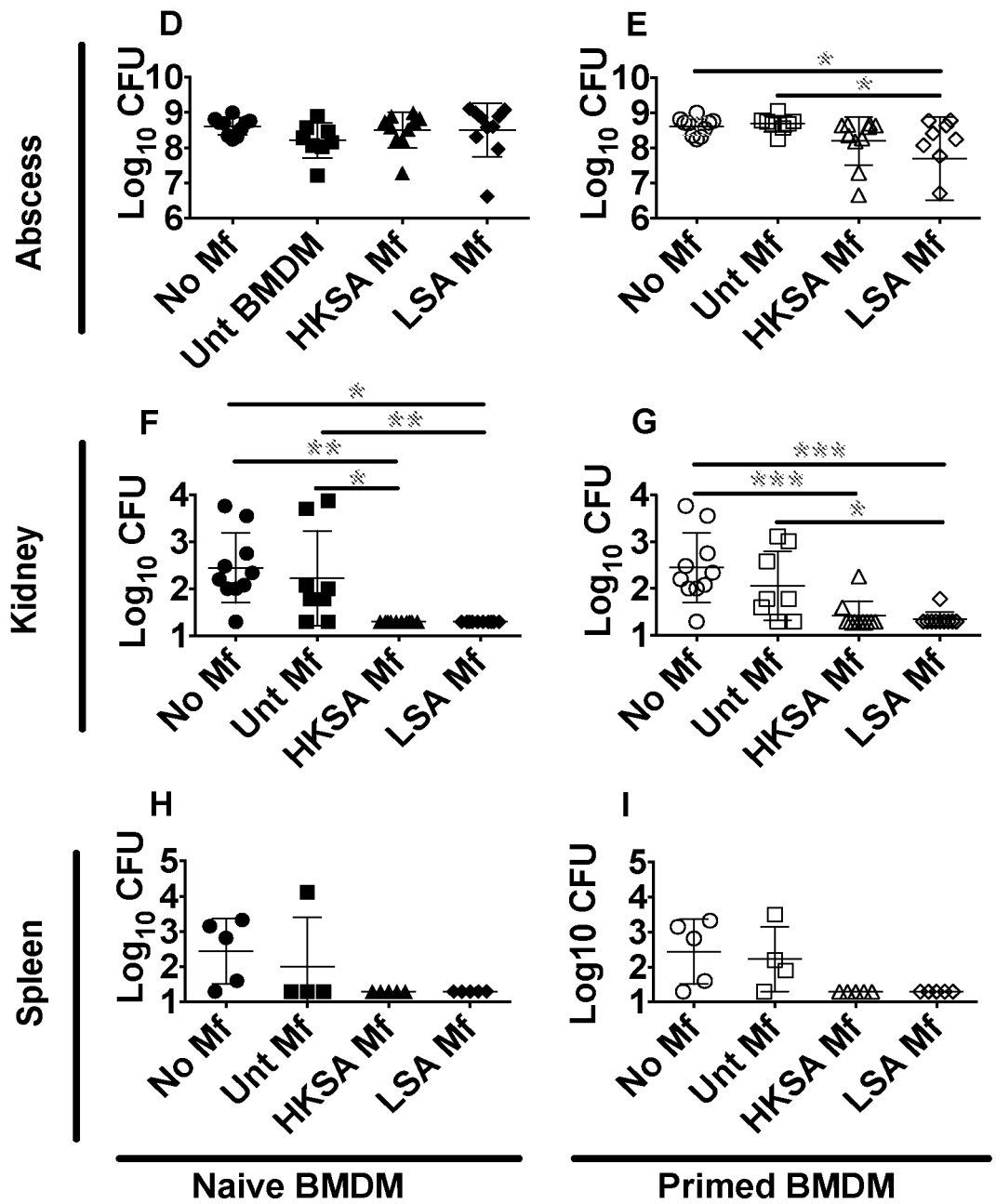
FIG. 6D-I

TARGET-PRIMED MACROPHAGES AND THERAPEUTIC USES THEREOF

CROSS REFERENCE TO RELATED APPLICATIONS

This application is a U.S. National Stage Application under 35 U.S.C. 371 of International Application No. PCT/US2019/051564, filed Sep. 17, 2019, which claims benefit under 35 U.S.C. § 119(e) to U.S. Provisional Patent Application No. 62/732,566, filed Sep. 17, 2018, the entire disclosure of each of which is hereby incorporated by reference.

BACKGROUND

*Staphylococcus aureus* is the most common cause of skin and skin structure infections (SSSI). Skin infection serves as a primary portal of entry for hematogenous dissemination. The high rate of recurring or persisting *S. aureus* infection in otherwise healthy individuals who have no known immune deficiencies or risk factors, and the lack of efficacy of conventional vaccines targeting this organism, have raised key questions regarding the determinants of protective immunity or immune memory versus this pathogen. The emergence of *S. aureus* resistant to many gold-standard antibiotics further compounds these issues. Thus, there is an urgent need to understand and apply novel approaches to inducing, stimulating or augmenting innate or adaptive immunity in defense against *S. aureus* infection.

SUMMARY

The present disclosure demonstrates the development of a method by which macrophages are primed in a manner that applies their innate immune memory capability for enhanced antimicrobial functions. The primed macrophages can then be administered for efficacy against infections such as those caused by *S. aureus*. Likewise, macrophages can be primed for anticancer uses.

The present disclosure, in some embodiments, provides a cell-based anti-infective and anticancer immunotherapy. Also provided is a cell-based anti-infective immunotherapy, a cell-based anticancer immunotherapy, a prophylactic immunotherapy, vaccine or therapeutic vaccine. The current data support the use of this technology to prevent or treat bacterial infection or cancer based on specific immune memory. By extension, the technology is broadly applicable to prevention or treatment of infections due to other organisms for which monocyte/macrophages may or may not normally afford protective immunity. The technology can be used in the presence or absence of other anti-infective drugs, such as antibiotics, and may be particularly useful in infections that are refractory to conventional antibiotics. The technology can also be used in the presence or absence of other anticancer drugs.

In some examples, monocyte/macrophages (Mo/Mf) are isolated from peripheral blood (PBMCs) or bone marrow of the intended autologous recipient host. These cells are then conditionally differentiated into macrophages and expanded ex vivo under conditions for optimal immune memory training with inactive (e.g. heat-killed or formalin-fixed) target organisms. This process can imbue the trained macrophages with antigen and/or target organism-specific memory. Thereafter, the trained cells are adoptively transferred into naïve or infected recipient host. The timing of administration could be preventive (e.g., prior to a known risk event such as a surgery, cancer chemotherapy, or like), to mitigate risk of recurrent infection, and/or as a therapeutic modality for the purpose of treatment intervention. Applications of this technology could be implemented with or without traditional anti-infective therapeutics or regimens, which may be additive or synergistic with this cell-based immunotherapy.

For cancer immunotherapy, the macrophages can be primed with tumor cells or tumor antigens. The primed cells can then be transferred into a cancer patient or a patient at risk of developing cancer. The treatment can be in combination with other anticancer agents.

In accordance with one embodiment of the present disclosure, provided is a method of preparing a population of target-primed macrophages, comprising culturing macrophages with a microorganism, in vitro or ex vivo, thereby yielding a population of target-primed macrophages.

In some embodiments, the macrophages have been prepared by isolating a monocyte or macrophage from a mammalian subject and differentiating or expanding the monocyte or macrophage. In some embodiments, the monocyte or macrophage is isolated from the peripheral blood or the bone marrow of the subject, wherein the subject is optionally not infected or immunized with the microorganism or is immunized with the microorganism.

In some embodiments, the microorganism is attenuated or inactivated, which is optionally heat-killed. In some embodiments, the inactivated microorganism is prepared as cellular homogenate or whole-cell preparation. In some embodiments, the microorganism is represented by specific native, synthetic, recombinant or otherwise isolated antigen or antigens.

In some embodiments, at least 50% of the target-primed macrophages in the population are polarized macrophages, preferably at least 60%, 70%, 75%, 80%, 85%, 90% or 95% of the target-primed macrophages in the population are polarized macrophages. In some embodiments, at least 50% of the target-primed macrophages in the population are M1-polarized macrophages, preferably at least 60%, 70%, 75%, 80%, 85%, 90% or 95% of the target-primed macrophages in the population are M1-polarized macrophages. In some embodiments, the M1-polarized macrophages have an immunophenotype signature of $CD38^+$ and $Egr2^-$. In some embodiments, the M1-polarized macrophages further express the $CD45^+$, $CD11Ly6G^-$, and $F4/80^+$ phenotypes. In some embodiments, no more than approximately 20% of the target-primed macrophages in the population are M2-polarized macrophages, which preferably are $CD38^-$ and $Egr2^+$, preferably no more than approximately 15%, 10%, 5%, 2% or 1% of the target-primed macrophages in the population are M2-polarized macrophages.

In some embodiments, the population of target-primed macrophages does not include B cell or T cell, or no more than about 10% of cells in the population are B cells or T cells, preferably no more than about 5%, 4%, 3%, 2% or 1% of cells in the population are B cells or T cells.

In some embodiments, the culturing is for a period up to 7 days, preferably from about 2 to 6 days, or from about 3 to 5 days, under physiological conditions. In some embodiments, the method further comprises removing the microorganism.

In some embodiments, the microorganism is selected from Table 1. In some embodiments, the microorganism comprises *S. aureus*. In some embodiments, the macrophages are human, bovine, canine or feline macrophages.

Provided, in one embodiment, is a composition comprising a population of target-primed macrophages, wherein at least 50% of the target-primed macrophages in the population are polarized macrophages, preferably at least 60%, 70%, 75%, 80%, 85%, 90% or 95% of the target-primed macrophages in the population are polarized macrophages.

In some embodiments, at least 50% of the target-primed macrophages in the population are M1-polarized macrophages, preferably at least 60%, 70%, 75%, 80%, 85%, 90% or 95% of the target-primed macrophages in the population are M1-polarized macrophages. In some embodiments, the M1-polarized macrophages express $CD38^+$ and $Egr2^-$ phenotypes. In some embodiments, the target-primed macrophages are primed in vitro or ex vivo.

Also provided, in one embodiment, is a composition comprising a population of target-primed macrophages prepared by a method of the present disclosure. In some embodiments, the composition further comprises an adjuvant and/or an antigen-adjuvant delivery system, preferably affiliated with nanoparticles. In some embodiments, the composition further comprises an anti-infective agent (e.g. antibiotic or anti-infective biologic), immune stimulant or cytokine (e.g. IFN-gamma), and/or a vaccine or immune-activating antigen.

Also provided, in one embodiment, is a method of preventing or treating infection by a microorganism in a mammalian subject in need thereof, comprising administering to the subject a composition of the present disclosure, wherein the administration is optionally local to infection by the microorganism. In some embodiments, the monocyte or macrophage has been isolated from the subject being treated. In some embodiments, the monocyte or macrophage has been isolated from a different subject from the subject being treated, and wherein the target-primed macrophages are HLA-matched with the subjected being treated.

In some embodiments, the subject suffers from a disease or condition selected from the group consisting of: skin infection including cellulitis, abscesses, necrotizing fasciitis, and other cutaneous infections, chronic infection including decubitus ulcer, diabetic foot, osteomyelitis, device or implant infections, systemic infection including bacteremia, metastatic abscesses in a target organ (e.g. kidney, liver, spleen), infections that are susceptible or resistant to conventional antibiotics, in the presence or absence of antibiotics, monomicrobial or polymicrobial infection, and/or infection in immunocompetent or immunodeficient, immunosuppressed or immunocompromised patients.

In some embodiments, the subject suffers from a disease or condition selected from Table 1.

In another embodiment, provided is a method of preparing a population of target-primed macrophages, comprising culturing macrophages with a tumor cell or a tumor antigen, in vitro or ex vivo, thereby yielding a population of target-primed macrophages.

In some embodiments, the macrophages have been prepared by isolating a monocyte or macrophage from a mammalian subject and differentiating or expanding the monocyte or macrophage. In some embodiments, the monocyte or macrophage is isolated from the peripheral blood or the bone marrow of the subject, wherein the subject optionally does not have the tumor, or has the tumor.

In some embodiments, the tumor cell or tumor antigen is isolated from a tumor sample, such as a tumor biopsy or circulating tumor cells (e.g. leukemia), which is optionally obtained from the same mammalian subject. In some embodiments, the tumor cell has been killed. In some embodiments, the tumor cell has been killed by heat.

In some embodiments, at least 50% of the target-primed macrophages in the population are polarized macrophages, preferably at least 60%, 70%, 75%, 80%, 85%, 90% or 95% of the target-primed macrophages in the population are polarized macrophages. In some embodiments, at least 50% of the target-primed macrophages in the population are M1-polarized macrophages, preferably at least 60%, 70%, 75%, 80%, 85%, 90% or 95% of the target-primed macrophages in the population are M1-polarized macrophages. In some embodiments, the M1-polarized macrophages have the immunophenotype signature of $CD38^+$ and $Egr2^-$. In some embodiments, the M1-polarized macrophages further express the $CD45^+$, $CD11Ly6G^-$, and F4/80+ phenotypes.

In some embodiments, no more than approximately 20% of the target-primed macrophages in the population are M2-polarized macrophages, which preferably are $CD38^-$ and $Egr2^+$, preferably no more than approximately 15%, 10%, 5%, 2% or 1% of the target-primed macrophages in the population are M2-polarized macrophages.

In some embodiments, the population of target-primed macrophages does not include B cell or T cell, or no more than about 10% of cells in the population are B cells or T cells, preferably no more than about 5%, 4%, 3%, 2% or 1% of cells in the population are B cells or T cells.

In some embodiments, the culturing is for a period up to 7 days, preferably from about 2 to 6 days, or from about 3 to 5 days, under physiological conditions. In some embodiments, the method further comprises removing the tumor cell or tumor antigen. In some embodiments, the tumor antigen is selected from the group consisting of EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, $\alpha V\beta 3$, $\alpha 5\beta 1$, ERBB2, ERBB3, MET, IGF1R, EPHA3, TRAILR1, TRAILR2, RANKL, FAP and Tenascin. In some embodiments, the macrophages are human, bovine, canine or feline macrophages.

In another embodiment, provided is a composition comprising a population of target-primed macrophages, wherein at least 50% of the target-primed macrophages in the population are polarized macrophages, preferably at least 60%, 70%, 75%, 80%, 85%, 90% or 95% of the target-primed macrophages in the population are polarized macrophages, and wherein the macrophages are primed with a tumor cell or tumor antigen.

In some embodiments, at least 50% of the target-primed macrophages in the population are M1-polarized macrophages, preferably at least 60%, 70%, 75%, 80%, 85%, 90% or 95% of the target-primed macrophages in the population are M1-polarized macrophages.

In some embodiments, the M1-polarized macrophages express $CD38^+$ and $Egr2^-$ phenotypes. In some embodiments, the target-primed macrophages are primed in vitro or ex vivo.

Also provided, in one embodiment, is a composition comprising a population of target-primed macrophages prepared by a method of the present disclosure. In some embodiments, the composition further comprises an adjuvant and/or an antigen-adjuvant delivery system, preferably affiliated with nanoparticles.

In some embodiments, the composition further comprises an anti-cancer biologic (e.g. checkpoint inhibitor), immune stimulant or cytokine (e.g. IFN-gamma), and/or a vaccine or immune-activating antigen.

In another embodiment, provided is a method of preventing or treating cancer by a microorganism in a mammalian subject in need thereof, comprising administering to the subject a composition of the present disclosure. In some embodiments, the monocyte or macrophage has been isolated from the subject being treated. In some embodiments, the monocyte or macrophage has been isolated from a different subject from the subject being treated, and wherein the target-primed macrophages are HLA-matched with the subjected being treated.

In some embodiments, the cancer is selected from the group consisting of those which may or may not be caused by infection, including stomach cancer bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, esophageal cancer, ovarian cancer, renal cancer, melanoma, prostate cancer and thyroid cancer.

BRIEF DESCRIPTION OF THE DRAWINGS

FIG. 1A-E. Priming affords protection during recurrent MRSA SSSI. Lesion sizes of naïve and primed male C576BL/6 mice (A) were measured at days 2 and 7. MRSA burden in abscesses (B), kidney (C), spleen (D) and liver (E) were quantified at days 2 and 7. Bacterial burden in abscess, kidney and spleen were quantified as CFU per abscess/organ. Burden in the liver was quantified as CFU per mg liver. *$P<0.05$, $P<0.01$, *$P<0.001$ using student's t-test. At least 4 mice per group were analyzed.

FIG. 5A-E. Primed bone marrow derived macrophages (BMDM) exhibit increased staphylocidal activity. Intracellular survival of bacteria in untreated (circles), heat-killed S. aureus (HKSA) treated (triangles) and live S. aureus (LSA) treated (squares) BMDM from naïve (filled symbols) and primed mice (open symbols) were measured 3 hours post-infection (multiplicity of infection 1:50). Naïve and primed BMDM were challenged with LAC [MRSA] (A), SH1000 [MSSA] (B), *Staphylococcus epidermidis* (C), *Enterococcus faecalis* (D) or *Escherichia coli* (E). *$P<0.05$, ***$P<0.001$ using two-way ANOVA. Data are presented as the average and standard deviation of points from a minimum of 2 independent experiments.

FIG. 6A-I. Adoptive transfer of primed BMDM recalled with LSA protects naïve mice from localized and disseminated MRSA SSSI. BMDM from naïve (filled symbols) and primed (open symbols) mice treated with PBS (squares), heat-killed S. aureus (HKSA) (triangles) or live S. aureus (LSA) (diamonds) was adoptively transferred into the skin of naïve mice. Four hours post-adoptive transfer, mice were incoculate with MRSA subcutaneously (SI Appendix, Figure S3B). Dermonecrosis area was measured at days 1, 3, 5 and 7 (A-C). Adoptive transfer of primed BMDM recalled with LSA resulted in smaller lesions compared to naïve BMDM recalled with LSA (A). Adoptive transfer of BMDM from primed (B) and naïve (C) mice (+/−SA treatment) were compared (red asterisk=LSA vs. no macrophage; black asterisk=LSA vs. untreated macrophage). At day 7, MRSA CFU was quantified from abscesses (D & E), kidneys (F & G) and spleens (H & I). *$P<0.05$, $P<0.01$, *$P<0.001$ using one-way ANOVA corrected for multiple comparison. At least 4 mice per group were analyzed.

DETAILED DESCRIPTION

Definitions

Figure 2A:
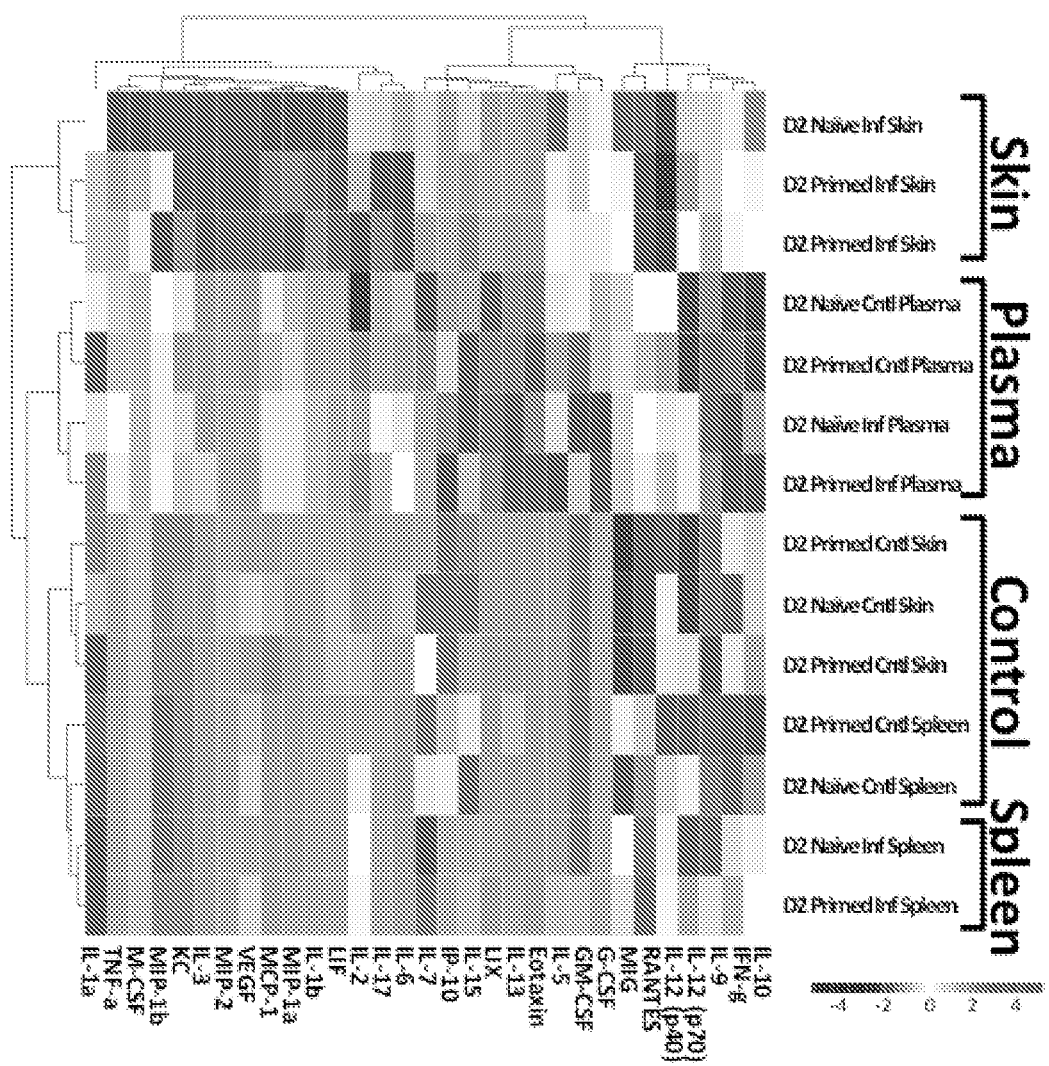
FIG. 2A-C. MRSA SSSI results in distinct cytokine signatures in specific tissue contexts. Cytokine levels in skin, spleen and plasma were analyzed using Luminex 32-plex assays. Data from day 2 (A), day 7 (B) and days 2 & 7 combined (C) were arranged via unsupervised clustering. Means of scaled values for each group were color-coded and plotted in heat maps. Unsupervised hierarchical clustering was performed on rows and columns using Euclidean distance as the similarity measure with Ward's linkage. At least 4 mice per group were analyzed.

The following description sets forth exemplary embodiments of the present technology. It should be recognized, however, that such description is not intended as a limitation on the scope of the present disclosure but is instead provided as a description of exemplary embodiments.

As used in the present specification, the following words, phrases and symbols are generally intended to have the meanings as set forth below, except to the extent that the context in which they are used indicates otherwise.

"Treatment" or "treating" is an approach for obtaining beneficial or desired results including clinical results. Beneficial or desired clinical results may include one or more of the following: a) inhibiting the disease or condition (e.g., decreasing one or more symptoms resulting from the disease or condition, and/or diminishing the extent of the disease or condition); b) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or c) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival.

"Prevention" or "preventing" means any treatment of a disease or condition that causes the clinical symptoms of the disease or condition not to develop or to develop in a manner that is mitigated as compared to the non-preventive state. The compositions may, in some embodiments, be administered to a subject (including a human) who is at risk or has a family history of the disease or condition.

"Subject" refers to an animal, such as a mammal (including a human), that has been or will be the object of prevention, treatment, observation or experiment. The methods described herein may be useful in human therapy and/or veterinary applications. In some embodiments, the subject is a mammal. In one embodiment, the subject is a human.

The term "therapeutically effective amount" or "effective amount" of a composition described herein means an amount sufficient to effect treatment when administered to a subject, to prevent or mitigate disease, provide a therapeutic benefit such as amelioration of symptoms or slowing of disease progression. For example, a therapeutically effective amount may be an amount sufficient to prevent or decrease a symptom of a disease or condition of infection or cancer. The therapeutically effective amount may vary depending on the subject, and disease or condition being treated, the weight and age of the subject, the severity of the disease or condition, and the manner of administering, which can readily be determined by one or ordinary skill in the art.

Target-Priming of Macrophages

The present disclosure relates to the target-priming of monocyte/macrophages (Mo/Mf) isolated from peripheral blood (PBMCs) or bone marrow. The monocyte or macrophages can be conditionally expanded ex vivo prior to target priming. The priming can be done with, e.g., inactive (e.g., heat-killed or formalin-fixed) target organisms or tumor cells. Such priming imbues the cells with antigen and/or target organism-specific or cancer-specific memory. Thereafter, the primed cells can be adoptively transferred into naïve or infected recipient host, or a cancer patient. The timing of administration could be preventive (e.g., prior to a known risk event such as a surgery, cancer chemotherapy, or like), to mitigate risk of recurrent infection, and/or as a therapeutic modality for the purpose of treatment intervention.

In accordance with one embodiment of the present disclosure, provided is a method of preparing a population of macrophages, such as target-primed macrophages.

As used herein, the term "target-primed macrophage," "primed macrophage," "activated macrophage," or "trained macrophage" refers to a macrophage cell that has been in contact with a target microorganism, a target tumor cell or a target tumor antigen. The target-primed macrophage can develop protective immune memory against the target microorganism, tumor cell or tumor antigen.

In some embodiments, the method entails culturing macrophages with a microorganism, in vitro or ex vivo, thereby yielding a population of target-primed macrophages. In some embodiments, the method entails culturing macrophages with a tumor cell or a tumor antigen, in vitro or ex vivo, thereby yielding a population of target-primed macrophages.

The macrophage, in some embodiments, can be prepared by isolating a monocyte or macrophage from a mammalian subject. In some embodiments, the isolated monocyte or macrophage is differentiated or expanded following isolation. In some embodiments, the monocyte or macrophage is isolated from the peripheral blood or the bone marrow of the subject. In some embodiments, the macrophages are human, bovine, canine or feline macrophages.

Examples of microorganisms are provided in Table 1. In one embodiment, the microorganism comprises *S. aureus*.

TABLE 1

Example microorganisms and associated diseases

| Infectious Disease | Microorganism Source |
|---|---|
| Acinetobacter infections | *Acinetobacter baumannii* |
| Actinomycosis | *Actinomyces israelii, Actinomyces gerencseriae* and *Propionibacterium propionicus* |
| African sleeping sickness (African trypanosomiasis) | *Trypanosoma brucei* |
| AIDS (Acquired immunodeficiency syndrome) | HIV (Human immunodeficiency virus) |
| Amebiasis | *Entamoeba histolytica* |
| Anaplasmosis | *Anaplasma* genus |
| Anthrax | *Bacillus anthracis* |
| Arcanobacterium haemolyticum infection | *Arcanobacterium haemolyticum* |
| Argentine hemorrhagic fever | Junin virus |
| Ascariasis | *Ascaris lumbricoides* |
| Aspergillosis | *Aspergillus* genus |
| Astrovirus infection | Astroviridae family |
| Babesiosis | *Babesia* genus |
| Bacillus cereus infection | *Bacillus cereus* |
| Bacterial pneumonia | multiple bacteria |
| Bacterial vaginosis (BV) | multiple bacteria |
| Bacteroides infection | *Bacteroides* genus |
| Balantidiasis | *Balantidium coli* |
| Baylisascaris infection | *Baylisascaris* genus |
| BK virus infection | BK virus |
| Black piedra | *Piedraia hortae* |
| Blastocystis hominis infection | *Blastocystis hominis* |
| Blastomycosis | *Blastomyces dermatitidis* |
| Bolivian hemorrhagic fever | Machupo virus |
| Borrelia infection | *Borrelia* genus |
| Botulism (and Infant botulism) | *Closfridium botulinum* |
| Brazilian hemorrhagic fever | Sabia |
| Brucellosis | *Brucella* genus |
| Burkholderia infection | usually *Burkholderia cepacia* and other *Burkholderia* species |
| Buruli ulcer | *Mycobacterium ulcerans* |
| Calicivirus infection (Norovirus and Sapovirus) | Caliciviridae family |

TABLE 1-continued

Example microorganisms and associated diseases

| Infectious Disease | Microorganism Source |
|---|---|
| Campylobacteriosis | *Campylobacter* genus |
| Candidiasis (Moniliasis; Thrush) | usually *Candida albicans* and other *Candida* species |
| Cat-scratch disease | *Bartonella henselae* |
| Cellulitis | usually Group A *Streptococcus* and *Staphylococcus* |
| Chagas Disease (American trypanosomiasis) | *Trypanosoma cruzi* |
| Chancroid | *Haemophilus ducreyi* |
| Chickenpox | Varicella zoster virus (VZV) |
| Chlamydia | *Chlamydia trachomatis* |
| Chlamydophila pneumoniae infection | *Chlamydophila pneumoniae* |
| Cholera | *Vibrio cholerae* |
| Chromoblastomycosis | usually *Fonsecaea pedrosoi* |
| Clonorchiasis | *Clonorchis sinensis* |
| Clostridium difficile infection | *Closfridium difficile* |
| Coccidioidomycosis | *Coccidioides immitis* and *Coccidioides posadasii* |
| Colorado tick fever (CTF) | Colorado tick fever virus (CTFV) |
| Common cold (Acute viral rhinopharyngitis; Acute coryza) | usually rhinoviruses and coronaviruses. |
| Creutzfeldt-Jakob disease (CJD) | CID prion |
| Crimean-Congo hemorrhagic fever (CCHF) | Crimean-Congo hemorrhagic fever virus |
| Cryptococcosis | *Cryptococcus neoformans* |
| Cryptosporidiosis | *Cryptosporidium* genus |
| Cutaneous larva migrans (CLM) | usually *Ancylostoma braziliense*; multiple other parasites |
| Cyclosporiasis | *Cyclospora cayetanensis* |
| Cysticercosis | *Taenia solium* |
| Cytomegalovirus infection | Cytomegalovirus |
| Dengue fever | Dengue viruses (DEN-1, DEN-2, DEN-3 and DEN-4) - Flaviviruses |
| Dientamoebiasis | *Dientamoeba fragilis* |
| Diphtheria | *Corynebacterium diphtheriae* |
| Diphyllobothriasis | *Diphyllobothrium* |
| Dracunculiasis | *Dracunculus medinensis* |
| Ebola hemorrhagic fever | Ebolavirus (EBOV) |
| Echinococcosis | *Echinococcus* genus |
| Ehrlichiosis | *Ehrlichia* genus |
| Enterobiasis (Pinworm infection) | *Enterobius vermicularis* |
| Enterococcus infection | *Enterococcus* genus |
| Enterovirus infection | *Enterovirus* genus |
| Epidemic typhus | *Rickettsia prowazekii* |
| Erythema infectiosum (Fifth disease) | Parvovirus B19 |
| Exanthem subitum (Sixth disease) | Human herpesvirus 6 (HHV-6) and Human herpesvirus 7 (HHV-7) |
| Fasciolopsiasis | *Fasciolopsis buski* |
| Fasciolosis | *Fasciola hepatica* and *Fasciola gigantica* |
| Fatal familial insomnia (FFI) | FFI prion |
| Filariasis | Filarioidea superfamily |
| Food poisoning by Clostridium perfringens | *Closfridium perfringens* |
| Free-living amebic infection | multiple |
| Fusobacterium infection | *Fusobacterium* genus |
| Gas gangrene (Clostridial myonecrosis) | usually *Clostridium perfringens*; other *Clostridium* species |
| Geotrichosis | *Geotrichum candidum* |
| Gerstmann-Sträussler-Scheinker syndrome (GSS) | GSS prion |
| Giardiasis | *Giardia intestinalis* |
| Glanders | *Burkholderia mallei* |
| Gnathostomiasis | *Gnathostoma spinigerum* and *Gnathostoma hispidum* |
| Gonorrhea | *Neisseria gonorrhoeae* |
| Granuloma inguinale (Donovanosis) | *Klebsiella granulomatis* |
| Group A streptococcal infection | *Streptococcus pyogenes* |
| Group B streptococcal infection | *Streptococcus agalactiae* |
| Haemophilus influenzae infection | *Haemophilus influenzae* |
| Hand, foot and mouth disease (HFMD) | Enteroviruses, mainly Coxsackie A virus and Enterovirus 71 (EV71) |
| Hantavirus Pulmonary Syndrome (HPS) | Sin Nombre virus |
| Helicobacter pylori infection | *Helicobacter pylori* |
| Hemolytic-uremic syndrome (HUS) | *Escherichia coli* 0157:H7, 0111 and 0104:H4 |
| Hemorrhagic fever with renal syndrome (HFRS) | Bunyaviridae family |
| Hepatitis A | Hepatitis A Virus |
| Hepatitis B | Hepatitis B Virus |
| Hepatitis C | Hepatitis C Virus |
| Hepatitis D | Hepatitis D Virus |
| Hepatitis E | Hepatitis E Virus |
| Herpes simplex | Herpes simplex virus 1 and 2 (HSV-1 and HSV-2) |

TABLE 1-continued

Example microorganisms and associated diseases

| Infectious Disease | Microorganism Source |
|---|---|
| Histoplasmosis | *Histoplasma capsulatum* |
| Hookworm infection | *Ancylostoma duodenale* and *Necator americanus* |
| Human bocavirus infection | Human bocavirus (HBoV) |
| Human ewingii ehrlichiosis | *Ehrlichia ewingii* |
| Human granulocytic anaplasmosis (HGA) | *Anaplasma phagocytophilum* |
| Human metapneumovirus infection | Human metapneumovirus (hMPV) |
| Human monocytic ehrlichiosis | *Ehrlichia chaffeensis* |
| Human papillomavirus (HPV) infection | Human papillomavirus (HPV) |
| Human parainfluenza virus infection | Human parainfluenza viruses (HPIV) |
| Hymenolepiasis | *Hymenolepis nana* and *Hymenolepis diminuta* |
| Epstein-Barr Virus Infectious Mononucleosis (Mono) | Epstein-Barr Virus (EBV) |
| Influenza (flu) | Orthomyxoviridae family |
| Isosporiasis | *Isospora belli* |
| Kawasaki disease | unknown; evidence supports that it is infectious |
| Keratitis | multiple |
| Kingella kingae infection | *Kingella kingae* |
| Kum | *Kuru prion* |
| Lassa fever | Lassa virus |
| Legionellosis (Legionnaires' disease) | *Legionella pneumophila* |
| Legionellosis (Pontiac fever) | *Legionella pneumophila* |
| Leishmaniasis | *Leishmania* genus |
| Leprosy | *Mycobacterium leprae* and *Mycobacterium lepromatosis* |
| Leptospirosis | *Leptospira* genus |
| Listeriosis | *Listeria monocytogenes* |
| Lyme disease (Lyme borreliosis) | usually *Borrelia burgdorferi* and other *Borrelia* species |
| Lymphatic filariasis (Elephantiasis) | *Wuchereria bancrofti* and *Brugia malayi* |
| Lymphocytic choriomeningitis | Lymphocytic choriomeningitis virus (LCMV) |
| Malaria | *Plasmodium* genus |
| Marburg hemorrhagic fever (MHF) | Marburg virus |
| Measles | Measles virus |
| Melioidosis (Whitmore's disease) | *Burkholderia pseudomallei* |
| Meningitis | multiple |
| Meningococcal disease | *Neisseria meningitidis* |
| Metagonimiasis | usually *Metagonimus yokagawai* |
| Methicillin-resistant Staphylococcus aureus (MRSA) | *Staphylococcus aureus* |
| Microsporidiosis | *Microsporidia* phylum |
| Molluscum contagiosum (MC) | Molluscum contagiosum virus (MCV) |
| Mumps | Mumps virus |
| Murine typhus (Endemic typhus) | *Rickettsia typhi* |
| Mycoplasma pneumonia | *Mycoplasma pneumoniae* |
| Mycetoma (Eumycetoma) | numerous species of bacteria (*Actinomycetoma*) and fungi |
| Myiasis | parasitic dipterous fly larvae |
| Neonatal conjunctivitis (Ophthalmia neonatorum) | most commonly *Chlamydia trachomatis* and *Neisseria gonorrhoeae* |
| (New) Variant Creutzfeldt-Jakob disease (vCJD, nvCJD) | vC, ID prion |
| Nocardiosis | usually *Nocardia asteroides* and other *Nocardia* species |
| Onchocerciasis (River blindness) | *Onchocerca volvulus* |
| Paracoccidioidomycosis (South American blastomycosis) | *Paracoccidioides brasiliensis* |
| Paragonimiasis | usually *Paragonimus westermani* and other *Paragonimus* species |
| Pasteurellosis | *Pasteurella* genus |
| Pediculosis capitis (Head lice) | *Pediculus humanus capitis* |
| Pediculosis corporis (Body lice) | *Pediculus humanus corporis* |
| Phthirus pubis Pediculosis pubis (Pubic lice, Crab lice) | |
| Pelvic inflammatory disease (PID) | multiple |
| Pertussis (Whooping cough) | *Bordetella pertussis* |
| Plague | *Yersinia pestis* |
| Pneumococcal infection | *Streptococcus pneumoniae* |
| Pneumocystis pneumonia (PCP) | *Pneumocystis jirovecii* |
| Pneumonia | multiple |
| Poliomyelitis | Poliovirus |
| Prevotella infection | *Prevotella* genus |
| Primary amoebic meningoencephalitis (PAM) | usually *Naegleria fowleri* |
| Progressive multifocal leukoencephalopathy | JC virus |
| Psittacosis | *Chlamydophila psittaci* |
| Q fever | *Coxiella burnetii* |
| Rabies | Rabies virus |
| Rat-bite fever | *Streptobacillus moniliformis* and *Spirillum minus* |

TABLE 1-continued

Example microorganisms and associated diseases

| Infectious Disease | Microorganism Source |
| --- | --- |
| Respiratory syncytial virus infection | Respiratory syncytial virus (RSV) |
| Rhinosporidiosis | *Rhinosporidium seeberi* |
| Rhinovirus infection | Rhinovirus |
| Rickettsial infection | *Rickettsia* genus |
| Rickettsialpox | *Rickettsia akari* |
| Rift Valley fever (RVF) | Rift Valley fever virus |
| Rocky mountain spotted fever (RMSF) | *Rickettsia rickettsii* |
| Rotavirus infection | Rotavirus |
| Rubella | Rubella virus |
| Salmonellosis | *Salmonella* genus |
| SARS (Severe Acute Respiratory Syndrome) | SARS coronavirus |
| Scabies | *Sarcoptes scabiei* |
| Schistosomiasis | *Schistosoma* genus |
| Sepsis | multiple |
| Shigellosis (Bacillary dysentery) | *Shigella* genus |
| Shingles (Herpes zoster) | Varicella zoster virus (VZV) |
| Smallpox (Variola) | Variola major or Variola minor |
| Sporotrichosis | *Sporothrix schenckii* |
| Staphylococcal food poisoning | *Staphylococcus* genus |
| Staphylococcal infection | *Staphylococcus* genus |
| Strongyloidiasis | *Strongyloides stercoralis* |
| Syphilis | *Treponema pallidum* |
| Taeniasis | *Taenia* genus |
| Tetanus (Lockjaw) | *Closfridium tetani* |
| Tinea barbae (Barber's itch) | usually *Trichophyton* genus |
| Tinea capitis (Ringworm of the Scalp) | usually *Trichophyton tonsurans* |
| Tinea corporis (Ringworm of the Body) | usually *Trichophyton* genus |
| Tinea cruris (Jock itch) | usually *Epidermophyton floccosum*, *Trichophyton rubrum*, and *Trichophyton mentagrophytes* |
| Tinea manuum (Ringworm of the Hand) | *Trichophyton rubrum* |
| Tinea nigra | usually *Hortaea werneckii* |
| Tinea pedis (Athlete's foot) | usually *Trichophyton* genus |
| Tinea unguium (Onychomycosis) | usually *Trichophyton* genus |
| Tinea versicolor (Pityriasis versicolor) | *Malassezia* genus |
| Toxocariasis (Ocular Larva Migrans (OLM)) | *Toxocara canis* or *Toxocara cati* |
| Toxocariasis (Visceral Larva Migrans (VLM)) | *Toxocara canis* or *Toxocara cati* |
| Toxoplasmosis | *Toxoplasma gondii* |
| Trichinellosis | *Trichinella spiralis* |
| Trichomoniasis | *Trichomonas vaginalis* |
| Trichuriasis (Whipworm infection) | *Trichuris frichiura* |
| Tuberculosis | usually *Mycobacterium tuberculosis* |
| Tularemia | *Francisella tularensis* |
| Ureaplasma urealyticum infection | *Ureaplasma urealyticum* |
| Venezuelan equine encephalitis | Venezuelan equine encephalitis virus |
| Venezuelan hemorrhagic fever | Guanarito virus |
| Viral pneumonia | multiple viruses |
| West Nile Fever | West Nile virus |
| White piedra (Tinea blanca) | *Trichosporon beigelii* |
| Yersinia pseudotuberculosis infection | *Yersinia pseudotuberculosis* |
| Yersiniosis | *Yersinia enterocolitica* |
| Yellow fever | Yellow fever virus |
| Zygomycosis | Alucorales order (Mucormycosis) and Entomophthorales order (Entomophthoramycosis) |

In some embodiments, the microorganism is attenuated or inactivated. Attenuation or inactivation can be done with methods known in the art, such as heat inactivation, chemical treatment (e.g., with antibiotics such as polymyxin), and genetic engineering (e.g., with mutation of genes). In some embodiments, the inactivated microorganism is prepared as cellular homogenate or whole-cell preparation. In some embodiments, the microorganism is represented by specific native, synthetic, recombinant or otherwise isolated antigen or antigens.

In some embodiments, the macrophages are cultured with a tumor cell or a tumor antigen. The tumor cell may be isolated from a tumor sample, such as a tumor biopsy or circulating tumor cells (e.g., leukemia). In some embodiments, the tumor cell has been killed, such as being killed by heat.

A "tumor antigen" is an antigenic substance produced in tumor cells. A tumor antigen may trigger an immune response in the host. Tumor antigens are useful in identifying tumor cells and are potential candidates for use in cancer therapy. Normal proteins in the body are not antigenic. Certain proteins, however, are produced or overexpressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-examples of tumor antigens include of EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

The target-priming of the present technology can prepare a population of macrophage cells useful for preventing and/or treating infectious diseases or cancer. In some embodiments, at least 50% of the target-primed macrophages in the population are polarized macrophages, preferably at least 60%, 70%, 75%, 80%, 85%, 90% or 95% of the target-primed macrophages in the population are polarized macrophages.

Examples of polarized macrophages include M1-polarized macrophages. In some embodiments, at least 50% of the target-primed macrophages in the population are M1-polarized macrophages, preferably at least 60%, 70%, 75%, 80%, 85%, 90% or 95% of the target-primed macrophages in the population are M1-polarized macrophages.

TABLE 2

Example markers of macrophage cells

| Macrophage cell | Markers |
|---|---|
| Non-specified macrophages | CD45+, CD11b+, Ly6G−, F4/80+ |
| M1-polarized macrophages | CD45+, CD11b+, Ly6G−, F4/80+, CD38+, Egr2− |
| M2-polarized macrophages | CD45+, CD11b+, Ly6G−, F4/80+, CD38−, Egr2+ |

Suitable markers for identifying M1-polarized macrophages include immunophenotype signature of CD38$^+$ and Egr2$^-$, in addition to CD45+, CD11b$^+$, Ly6G$^-$, and F4/80$^+$ phenotypes (see Table 2).

In some embodiments, the population includes no more than approximately 20%, preferably no more than approximately 15%, 10%, 5%, 2% or 1%, M2-polarized macrophages. M2-polarized macrophages have phenotypes of CD38$^-$ and Egr2$^+$.

In some embodiments, the population of target-primed macrophages does not include B cell or T cell, or no more than about 10% of cells in the population are B cells or T cells, preferably no more than about 5%, 4%, 3%, 2% or 1% of cells in the population are B cells or T cells.

Culturing of the macrophages can be for a period up to 7 days, preferably from about 2 to 6 days, or from about 3 to 5 days, under physiological conditions.

Once the macrophages are target-primed, the microorganisms, tumor cells or tumor antigen can be optionally removed from the sample.

Target-Primed Macrophages and Uses

Also provided, in some embodiments, are compositions that include the macrophages prepared according to a method of the present disclosure and their uses.

In some embodiments, provided is a composition comprising a population of target-primed macrophages, wherein at least 50% of the target-primed macrophages in the population are polarized macrophages. In some embodiments, at least 60%, 70%, 75%, 80%, 85%, 90% or 95% of the target-primed macrophages in the population are polarized macrophages.

In some embodiments, at least 50% of the target-primed macrophages in the population are M1-polarized macrophages. In some embodiments, at least 60%, 70%, 75%, 80%, 85%, 90% or 95% of the target-primed macrophages in the population are M1-polarized macrophages.

In some embodiments, the composition further includes an adjuvant and/or is provided with an antigen-adjuvant delivery system. Such agents can be affiliated with nanoparticles. In some embodiment, the composition further includes an anti-infective agent (e.g., antibiotic or anti-infective biologic), immune stimulant or cytokine (e.g., IFN-gamma), and/or a vaccine or immune-activating antigen.

In some embodiments, the composition further includes an anticancer agent, or can be administered separately from an anticancer agent. Non-limiting examples include antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the disclosure can further include, or can be administered in combination with cytokines. Cytokines that may be administered with the compositions of the disclosure include, but are not limited to, IL-2, IL-3, IL-4, IL-5, IL-6, IL-7, IL-10, IL-12, IL-13, IL-15, anti-CD40, CD40L, and TNF-α.

Methods of treatments or preventive uses are also provided, as long as associated manufacturing methods and medicaments. In one embodiment, provided is a method of preventing or treating infection by a microorganism in a mammalian subject in need thereof, comprising administering to the subject a target-primed macrophage. In some embodiments, the administration is local to the infection/cancer, or is at risk of being infected.

In some embodiments, the monocyte or macrophage used to prepare the target-primed macrophage is isolated from the subject being treated. In some embodiments, the subject being treated suffers from or is at risk of developing an infection with the microorganism used to prime the macrophage.

In some embodiments, the monocyte or macrophage is isolated from a different subject from the subject being treated, but the target-primed macrophages are HLA-matched with the subjected being treated. In some embodiments, the subject being treated suffers from or is at risk of developing an infection with the microorganism used to prime the macrophage.

In some embodiments, the subject suffers from or is at risk of developing a disease or condition selected from the group consisting of skin infection including cellulitis, abscesses, necrotizing fasciitis, and other cutaneous infections, chronic infection including decubitus ulcer, diabetic foot, osteomyelitis, device or implant infections, systemic infection including bacteremia, metastatic abscesses in a target organ (e.g., kidney, liver, spleen), infections that are susceptible or resistant to conventional antibiotics, in the presence or absence of antibiotics, monomicrobial or polymicrobial infection, and/or infection in immunocompetent or immunodeficient, immunosuppressed or immunocompromised patients. In some embodiments, the subject suffers from a disease or condition selected from Table 1.

In some embodiments, the subject suffers from cancer. In some embodiments, the cancer is selected from the group consisting of those which may or may not be caused by infection, including stomach cancer bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, esophageal cancer, ovarian cancer, renal cancer, melanoma, prostate cancer and thyroid cancer.

In some embodiments, the monocyte or macrophage used to prepare the target-primed macrophage is isolated from the subject being treated. In some embodiments, the tumor cell or tumor antigen is also isolated from the subject being treated. In some embodiment, the subject has a tumor cell that also expresses the tumor antigen used to prime the macrophage. In some embodiments, the subject being treated suffers from or is at risk of developing a tumor of the same type as the tumor cell or tumor antigen used to prime the macrophage.

In some embodiments, the monocyte or macrophage is isolated from a different subject from the subject being treated, but the target-primed macrophages are HLA-matched with the subjected being treated. In some embodiments, the subject being treated suffers from or is at risk of developing a tumor of the same type as the tumor cell or tumor antigen used to prime the macrophage.

Compositions and Modes of Administration

The compositions may be administered in either single or multiple doses. The pharmaceutical composition may be administered by various methods including, for example, rectal, buccal, intranasal and transdermal routes. In certain embodiments, the pharmaceutical composition may be administered by intra-arterial injection, intravenously, intraperitoneally, parenterally, intramuscularly, subcutaneously, orally, topically, or as an inhalant.

One mode for administration is parenteral, for example, by intravenous or intra-arterial injection. The forms in which the pharmaceutical compositions described herein may be incorporated for administration by injection include, for example, cell culture medium, or a sterile aqueous solution, and similar pharmaceutical vehicles.

Another mode of administration may be, for example, subcutaneous injection at the site of infection.

Another mode of administration may be, for example, introduction into a surgical, device implantation or other internal site by direct (e.g. during open surgical procedure) or indirect means (e.g. by way of endoscope, catheter, transcutaneous infection, etc).

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

Example 1

Protective Immunity in Recurrent *Staphylococcus aureus* Infection Reflects Localized Immune Signatures and Macrophage-Conferred Memory Methods Bacterial Strains and Preparation This study utilized methicillin-resistant *S. aureus* (MRSA) strain LAC, a USA300 strain isolated from an outbreak at the Los Angeles County Jail and the phenotypic and genotypic profile of this strain has been thoroughly characterized previously. Studies also included methicillin-sensitive *S. aureus* strain SH1000 [a well-characterized laboratory strain], *Staphylococcus epidermidis* (ATCC 12228), *Enterococcus faecalis* (ATCC 29212), or *Escherichia coli* (ATCC 43889). Bacteria were cultured from virulence-validated master cell banks and grown to log-phase in BHI medium at 37° C. Resulting cells were harvested, washed, suspended in PBS, sonicated, quantified by spectrophotometry and diluted to the desired CFU in PBS or RPMI for use in vitro or in vivo. To generate heat-killed LAC, bacteria were prepared as described above and boiled for 30 minutes.

Mouse of Model of Recurrent SSSI

Animal studies were performed in accordance with approved animal use policies of Los Angeles Biomedical Research Institute at Harbor-UCLA following NIH guidelines. Male C57BL/6 (WT) mice (20-25 grams; Jackson Labs, Sacramento, CA) were studied using a subcutaneous SSSI model. For primary infection, SSSI was established via inoculation with ~1×10$^7$ CFU MRSA in 100 µl PBS by subcutaneous injection into the right flank. Control animals received an identical volume of PBS buffer alone. In infected animals, abscesses formed along with corresponding dermonecrosis as anticipated, and were then permitted to completely resolve over 6 weeks. For recurring SSSI, the same previously infected (primed) mice were then re-infected using an identical regimen in both the right and left flanks (6 weeks post initial infection). Lesions were analyzed over the study period. At days 2 or 7 post-infection, the mice were humanely euthanized for tissue analysis.

Skin Lesion Severity

Dermonecrosis areas of each flank were measured in every mouse over the post-challenge study periods. To do so, mice were anesthetized and the dermonecrosis area (mm$^2$; lesion length [l] and width [w]) was quantified for each lesion as previously reported.

MRSA Tissue Burden

At the 2- or 7-day study endpoint, mice were euthanized and skin abscesses, kidneys, spleen and liver were enumerated ex vivo via colony forming units (CFU) after overnight culture on plates (lower limit of detection=20 CFU/sample). In parallel, a portion of tissue homogenate was reserved for cytokine analysis as detailed below.

Luminex xMAP Immunoassay

Mouse 32-plex magnetic cytokine/chemokine kits (EMD Millipore) were used per manufacturer's instructions and fluorescence quantified using Luminex 200™ instrument by the UCLA Immune Assessment Core. Cytokine/chemokine concentrations were calculated using Milliplex Analyst software version 4.2 (EMD Millipore). Tissue homogenates were normalized by total protein content to 330 ug/ml by Coomassie Protein Assay Kit (Thermo Scientific).

Cytokine Heat Maps

For hierarchical clustering analysis, analyte abundances irrespective of conditions were normalized using Z-scaling. Then, means of scaled values for each group were color-coded and plotted in heat maps. Unsupervised hierarchical clustering was performed on rows and columns using Euclidean distance as the similarity measure with Ward's linkage. R version 3.3.1 was used.

Immune Cell Subset Profiles

Inguinal lymph nodes and spleen of each mouse were mechanically dissociated and cell isolated. Skin abscesses were processed and cells isolated per protocol. Briefly, skin abscesses were aseptically dissected and placed into skin isolation buffer (HBSS, 10% FBS, 5 mM EDTA, 10 mM HEPES) for 30 minutes at 150 rpm. Abscesses were placed into fresh media containing collagenase D, chopped and incubated for 30 minutes at 150 rpm. Skin fragments were removed and cells isolated from media. Cells were stained with fluorochrome-conjugated antibodies and analyzed by multi-color flow cytometric analysis using an LSRII cytometer (Becton-Dickinson). Intranuclear molecules were accessed for staining using an established protocol for cell permeabilization (Thermo Fisher).

Bone Marrow Derived Macrophages (BMDM)

Bone marrow derived macrophages were differentiated as previously described. Briefly, bone marrow cells were isolated from femurs and tibias of naïve or primed WT mice. Cells were differentiated in BMDM media (DMEM/F12, 10% FBS, 25 mM L-glutamate, penicillin/streptomycin, 500 U/ml recombinant mouse M-CSF [Biolegend]). On day 10, cells were challenged with heat-killed MRSA or live MRSA (Multiplicity of Infection [MOI]1:1) and permitted to acclimate for 4 days. The BMDM were used on day 14.

BMDM Intracellular Survival Assay

The BMDM ($5 \times 10^5$ cells) were plated on sterile 18 mm glass cover slips and challenged with MRSA. After 30 minutes, gentamicin (50 μg/ml final concentration) was added to kill extracellular bacteria. At indicated time points, BMDM were lysed and surviving MRSA CFU were enumerated after overnight culture on plates.

Macrophage Adoptive Transfer in MRSA SSSI

The BMDM ($\sim 5 \times 10^5$ BMDM/100 μl) were adoptively transferred into the right flank of naïve WT mice. Control animals received media alone. Four hours post-adoptive transfer, SSSI was established via inoculation with $\sim 1 \times 10^7$ CFU of MRSA by subcutaneous injection into both flanks. Lesions were monitored over 7 days, at which point the mice were euthanized and the abscesses were excised for quantitative culture.

Statistical Analyses

Differences in experimental results were compared by ANOVA or Student's t-test as indicated. Data analyzed by GraphPad Prism software and reported as mean±standard deviation. P-values of <0.05 were considered statistically significant.

Results

Immune Protection Differs in Local Versus Disseminated Infection

Priming resulted in localized protection as evidenced by smaller skin lesions over the course of infection as compared to naïve-infected controls (FIG. 1A). In primed mice, MRSA burden in skin lesions was similar to naïve mice at day 2, but was significantly reduced by day 7. Importantly, while priming achieved protection in both flanks at day 7, lesions on the flank previously infected had the greatest reduction in severity. Priming initially increased the MRSA burden of the kidney and spleen at day 2, but then reduced it in these organs and the liver by day 7 (FIG. 1B-E). Thus, priming enhances the eventual control of infection in the target organs. Collectively, these results suggest that priming affords protective immunity that is targeted, and manifests at later time points in the evolution of the infection.

Cytokine Signatures of Protection Differ in Spatial Contexts

Figure 2B:
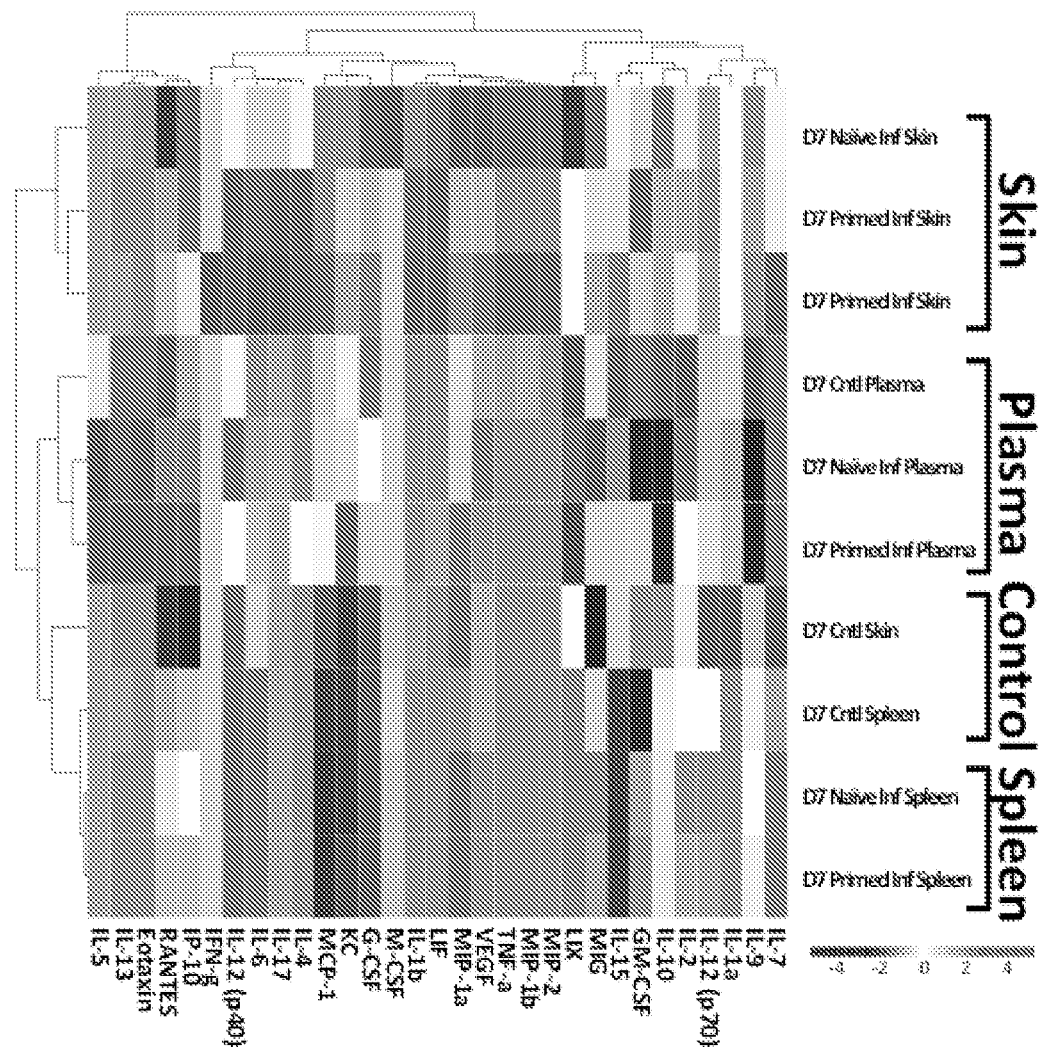
Figure 2C:
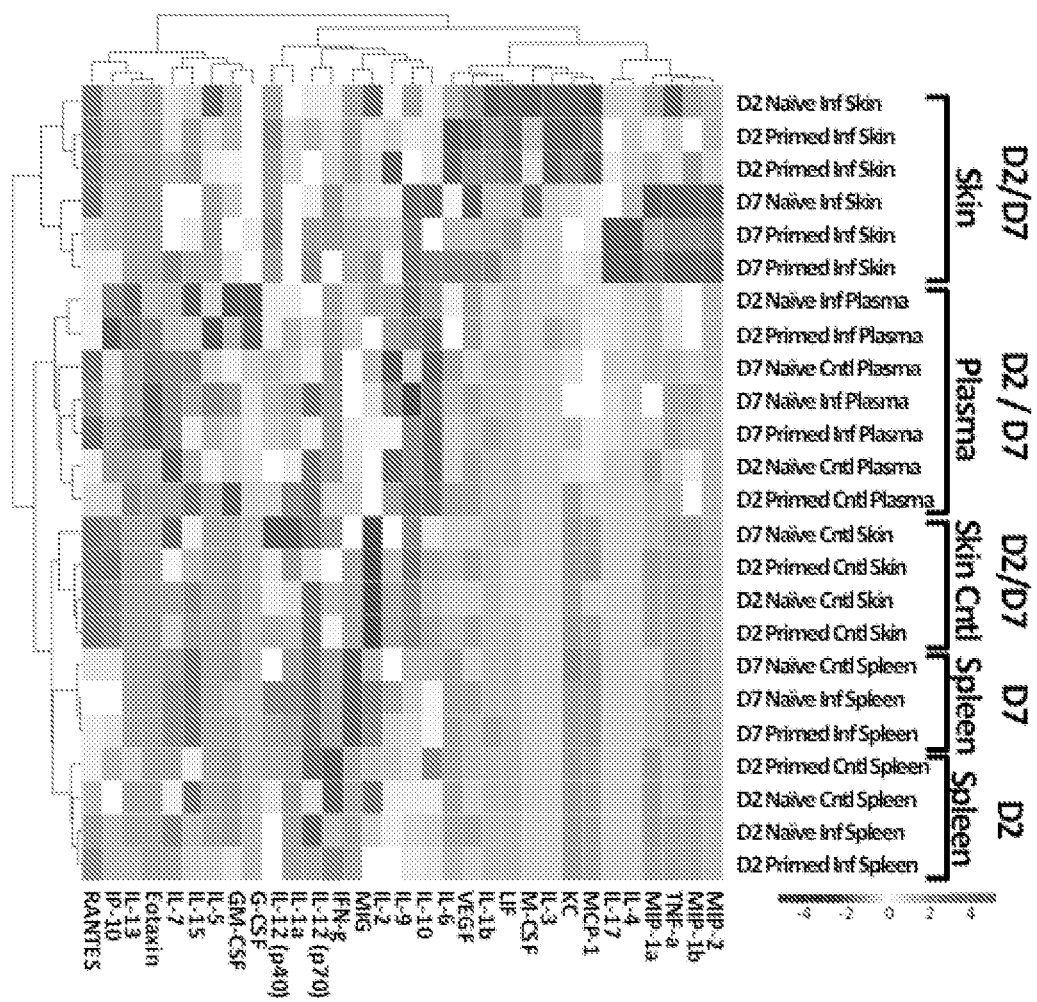

Unsupervised proteomic analyses comparing cytokine patterns in skin, plasma and spleen revealed distinct patterns during MRSA SSSI and invasive infection at day 2 vs. day 7. These patterns clustered into 4 groups: skin, plasma, spleen and uninfected control skin (FIG. 2A-C). In this analysis, the primed mice clustered with the naïve mice. As expected, uninfected control mice had minimal variations in the expression of most cytokines or chemokines detected. In supervised analyses, infection in skin resulted in increased pro-inflammatory cytokines (e.g. IL-1β, IL-6, TNF-α), chemokines (e.g. MIP-1α/β, MIP-2, KC) and markers of proliferation or differentiation (e.g. G-CSF, VEGF), as compared to spleen or plasma. Notably, no specific pattern of IFN-γ response was detected. In comparison to skin, no specific patterns of cytokine responses were observed in the spleen or blood. These results suggest that protective cytokine signatures are distinct for specific tissues during MRSA SSSI.

Figure 3A:
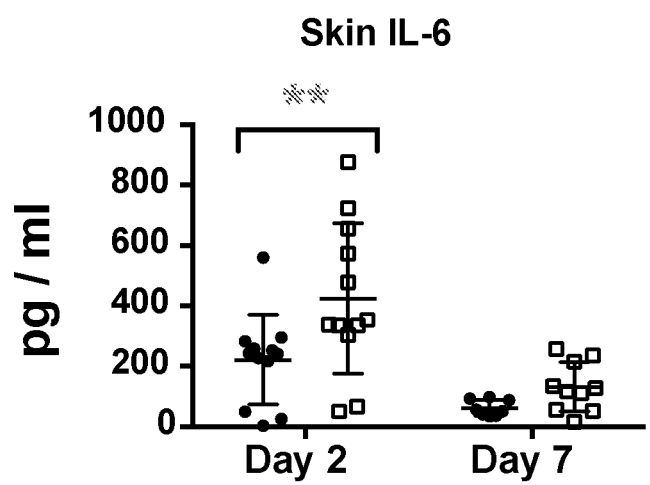
FIG. 3A-F. Priming induces different cytokine responses in abscesses vs. blood vs. spleen during recurrent MRSA SSSI. Priming induced the expression of IL-6 and MIG in abscess at day 2 (A, D) while IL-17, RANTES and MIG expressions were increased at day 7 (B-D). In comparison, priming induced IP-10 expression in plasma (E). Conversely, IL-9 expression in the spleen was decreased (F) at day 2. All other cytokines measured showed no difference between naïve and primed groups. *$P<0.05$, **$P<0.01$ using Two-way ANOVA.
Figure 3B:
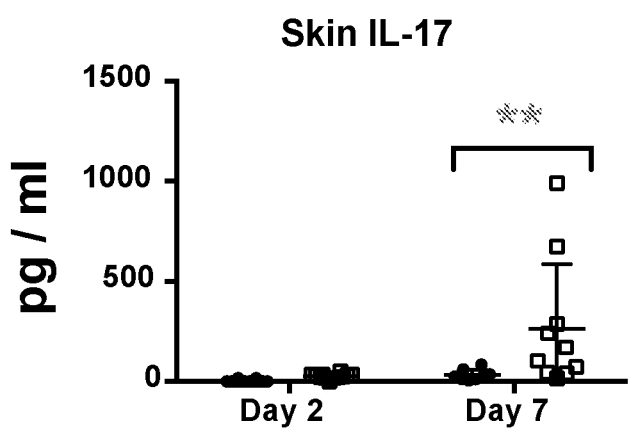
Figure 3C:
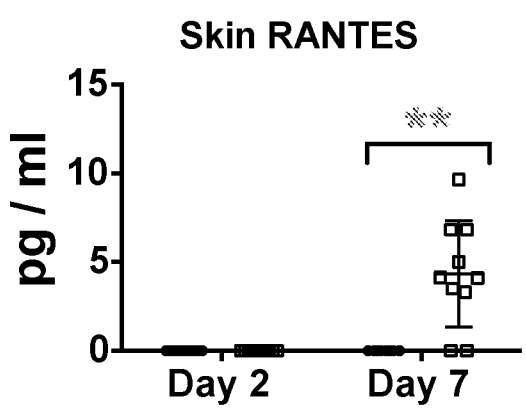
Figure 3D:
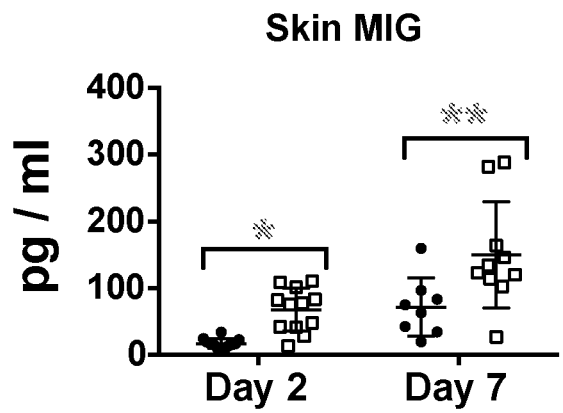
Figure 3E:
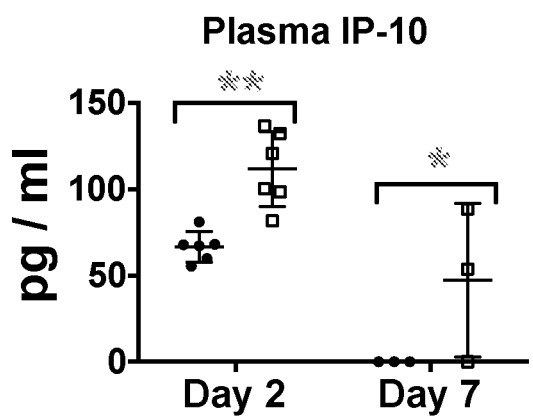
Figure 3F:
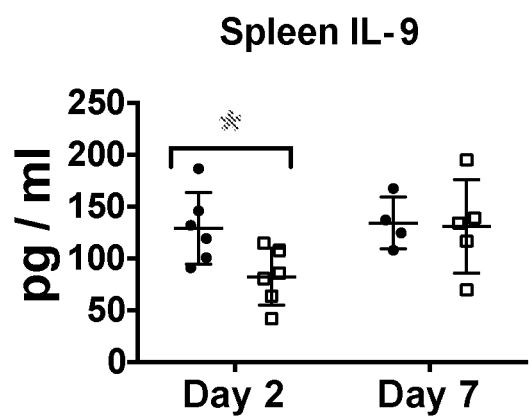

Priming Induces Specific Cytokine Signatures Corresponding to Protective Immunity Specific cytokine signatures correlated with protective immunity. In skin, priming resulted in increased IL-6 expression at day 2, followed by increased IL-17 expression at day 7 (FIGS. 3A & B). Additionally, priming led to increased MIG and RANTES in skin at day 7, cytokines that are involved in T cell recruitment and maintenance (FIGS. 3C & D). During disseminated infection, priming resulted in decreased IL-9 in the spleen and increased IP-10 in the plasma (FIGS. 3E & F). These results support a central role for Th17 responses in protective immunity of the skin, but not in hematogenous dissemination. More broadly, this pattern of findings is consistent with the hypothesis that protective immunity to MRSA involves molecular signals that correspond to specific tissue context and progression of infection.

Cellular Signatures of Protection Differ in Tissue-Specific Contexts

Figure 4A:
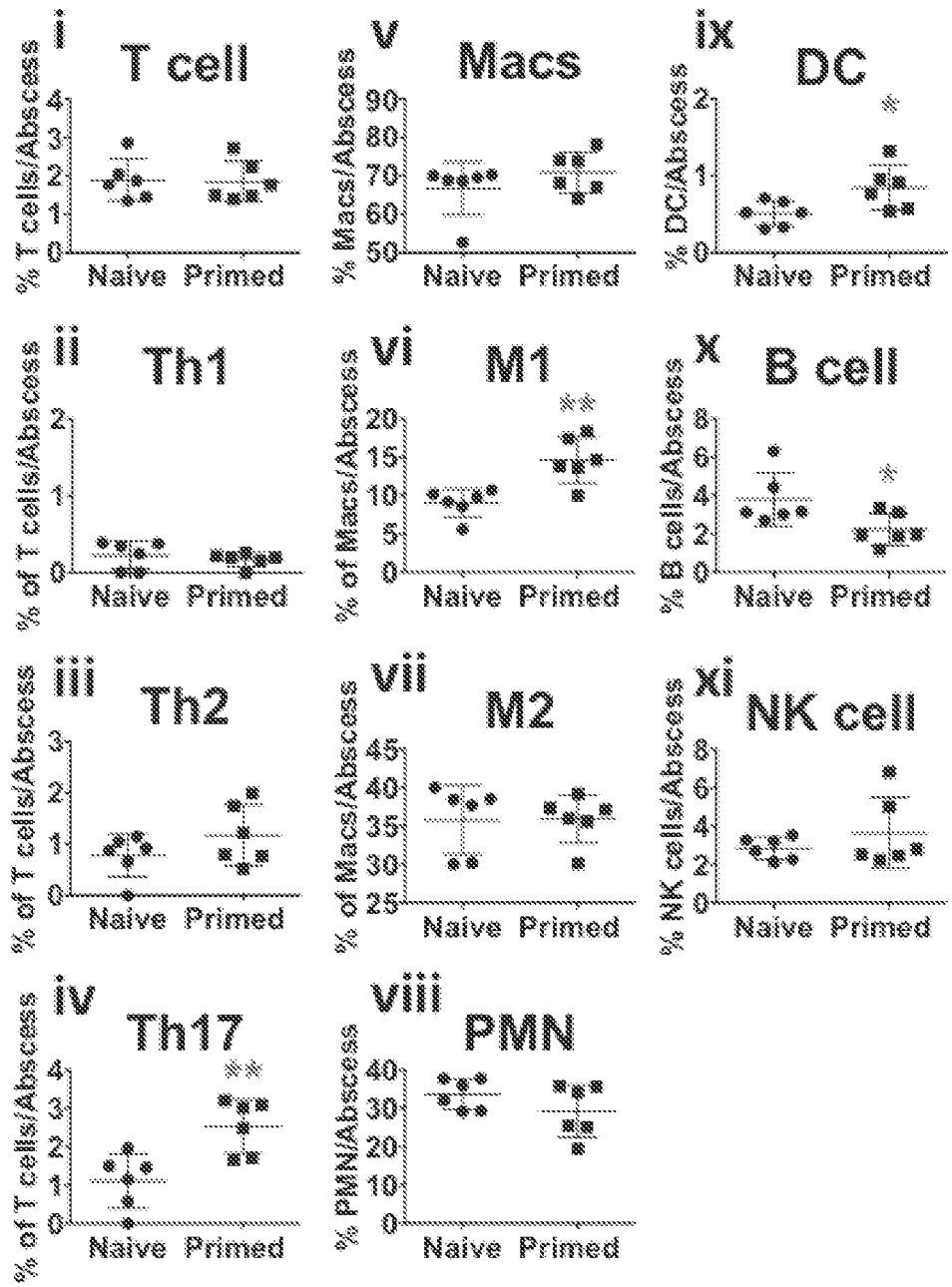
FIG. 4A-C. Priming induces distinct changes in localized cell populations during recurrent MRSA SSSI. T cell, macrophage, neutrophil (PMN), dendritic cell (DC), B cell and natural killer (NK) cell populations were analyzed and expressed as percent of total CD45$^+$ cells in the skin (A) and draining inguinal lymph nodes (B). T cell subsets (Th1, Th2 and Th17) were expressed as percent of total CD3$^+$ T cells. Macrophage subsets (M1 and M2) were expressed as proportion of total macrophages. *$P<0.05$, **$P<0.01$ using student's t-test. At least 6 samples per group were analyzed. (C) Priming did not induce changes in splenic cell populations during recurrent MRSA SSSI. Cell populations were analyzed and expressed as percent of total popula8on in the spleen. N=3 samples per group.

Cellular responses were analyzed at day 7 during recurrent MRSA infection, as this later time point corresponded with protection observed in primed mice (FIG. 1). Priming caused an increase of M1 macrophage and dendritic cell populations in skin abscesses, but a decrease in the total B cell population in skin (FIG. 4A). Concordant with increased IL-17 expression in skin abscesses, priming also increased the relative proportion of Th17 cells in skin, but not that of Th1 or Th2 cells, as compared to naïve controls (FIG. 4A). Priming did not significantly change M2 macrophage, neutrophil or NK cell populations in abscesses (FIG. 4A).

Figure 4B:
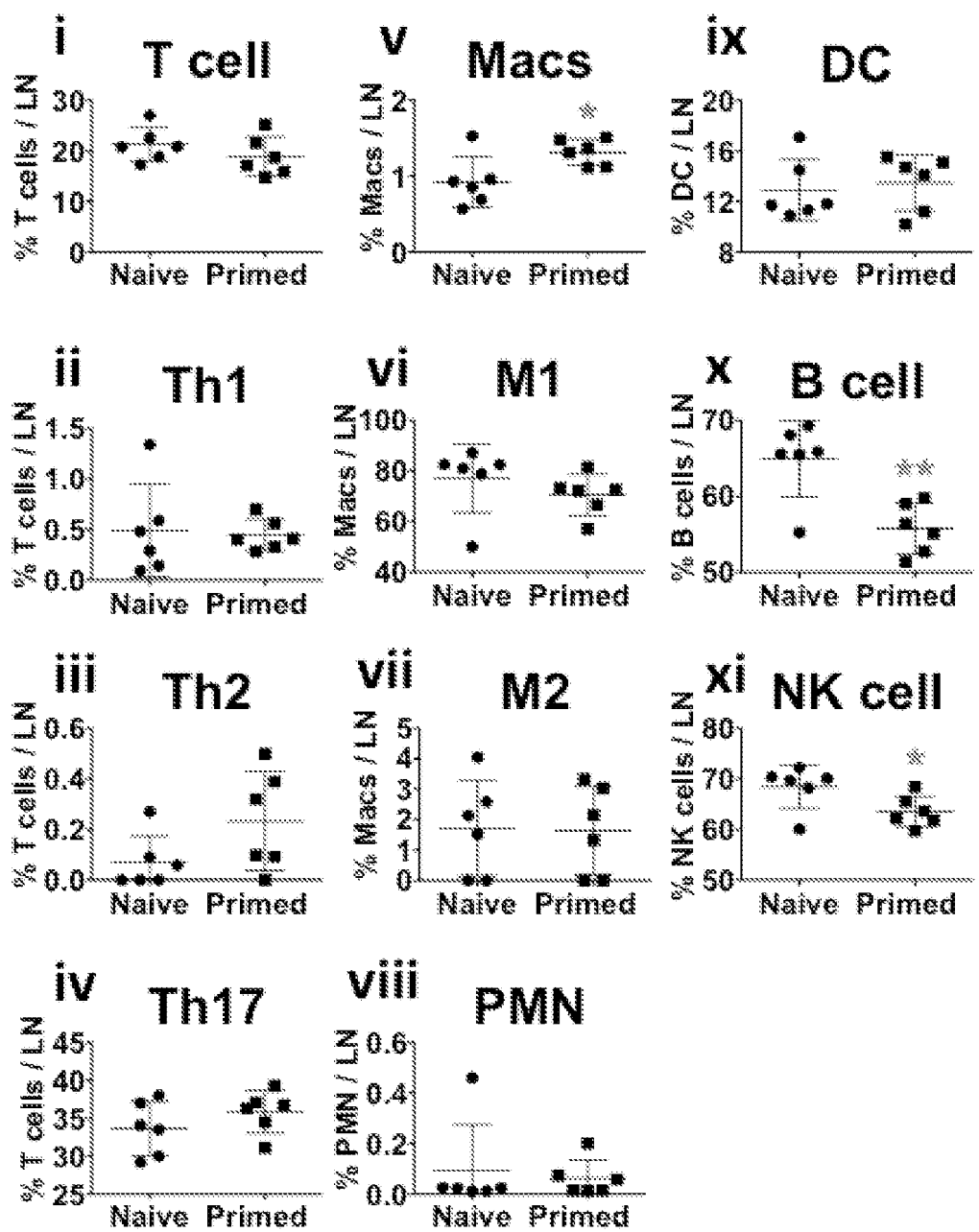
Figure 4C:
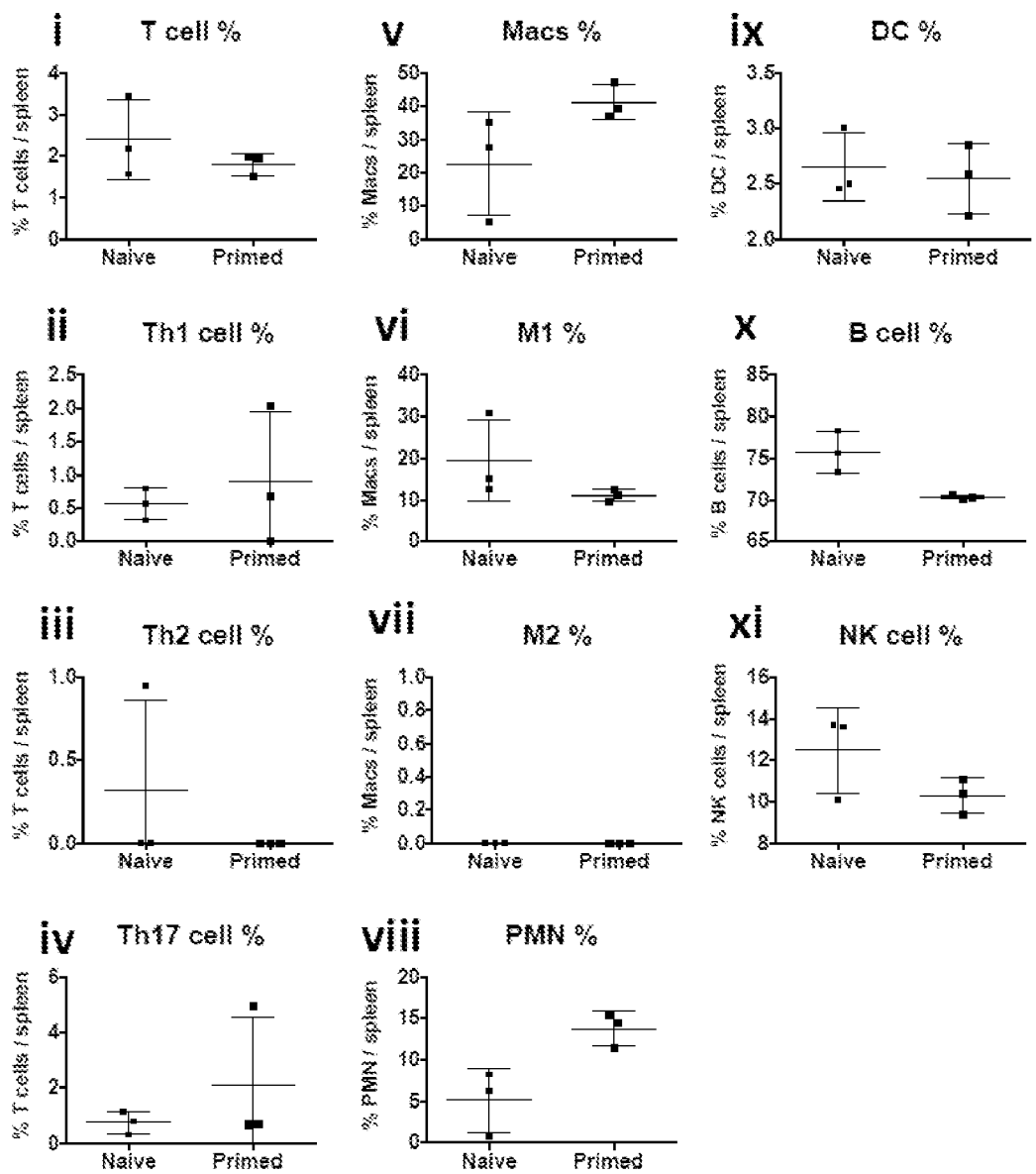

Consistent with localized responses in the skin, draining inguinal lymph nodes (iLN) had an increased total macrophage population, but decreased B and NK cell populations (FIG. 4B). No significant changes were found in total T cell, PMN, or DC populations in the iLN of primed vs. naïve groups (FIG. 4B). Similar to cytokine results, no significant differences were detected in cell populations in the spleens of primed vs. naïve mice (FIG. 4C).

Macrophages Confer Protective Immunity Against MRSA

The preceding results suggested macrophages present in the skin and iLN of primed mice may be involved in protective immune memory against MRSA. To investigate this hypothesis, the role of bone-marrow derived macrophages (BMDM) from naïve and primed mice were analyzed using in vitro and in vivo models.

A. Priming Increases Macrophage Staphylocidal Activity In Vitro

Figure 5A:
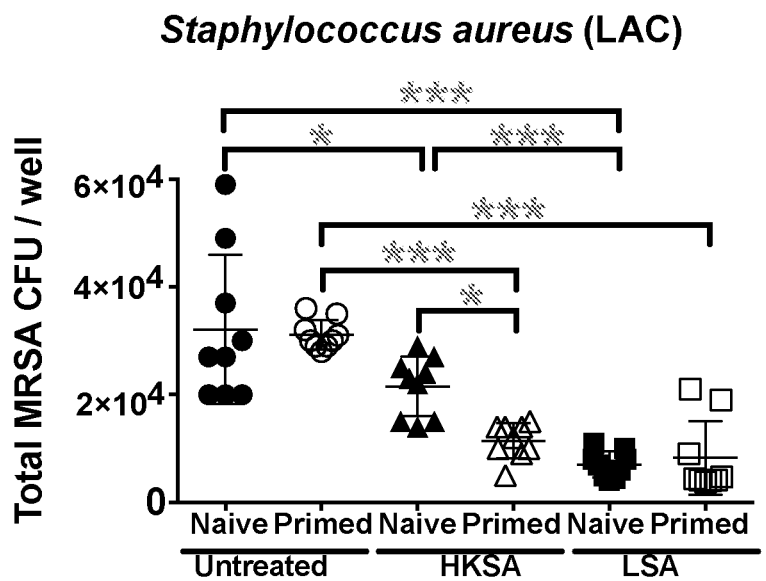
Figure 5B:
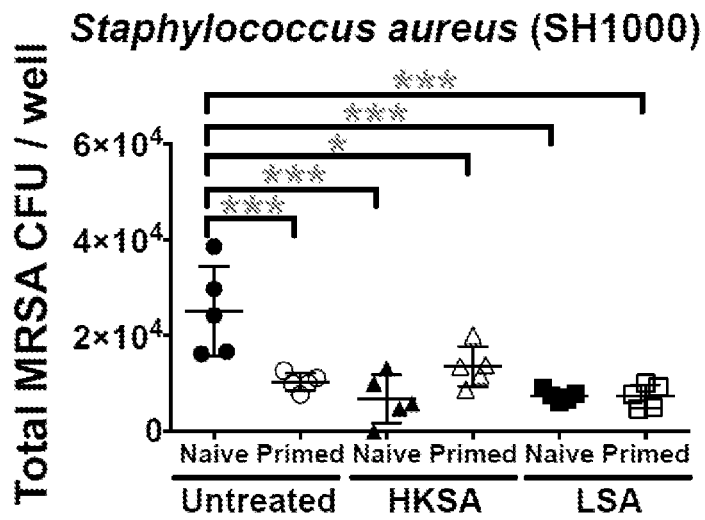

First, BMDM from naïve and primed mice were compared for their capacity to phagocytose and kill S. aureus with and without recall exposure to S. aureus. Phagocytosis of MRSA by BMDM from naïve and primed animals with and without exposure to S. aureus was equivalent. However, staphylocidal activity was greater in BMDM from primed mice versus naïve mice as measured by survival of intracellular MRSA, if pre-exposed to heat-killed S. aureus (HKSA) (FIG. 5A). Interestingly, primed and naïve BMDMs pre-exposed to live S. aureus (LSA) were equivalent in their capacity to kill MRSA, as pre-exposure to LSA induced near maximal MRSA killing in BMDM. Further, pre-exposure of BMDM to HKSA or LSA resulted in lower intracellular MRSA survival as compared to untreated BMDM (FIG. 5A). Next, primed and naïve BMDM were tested for specific killing against comparative staphylococci, Gram-positive and Gram-negative bacteria. Interestingly, BMDM primed with LAC-USA300 also exerted greater staphylocidal activity against a distinct S. aureus strain (SH1000) compared to untreated naïve BMDM (FIG. 5B). This protection was specific to S. aureus, as priming with S. aureus did not enhance macrophage efficacy against Staphylococcus epidermidis (distinct staphylococcal species), Enterococcus faecalis (Gram-positive bacterium of different genus) or Escherichia coli (Gram-negative bacterium) (FIG. 5C-E). These in vitro data support that priming of BMDM during in vivo infection affords greater anti-staphylococcal activity specifically on recall to S. aureus.

B. Adoptive Transfer of Primed Macrophages Confers Protective Immunity In Vivo

Figure 6A:
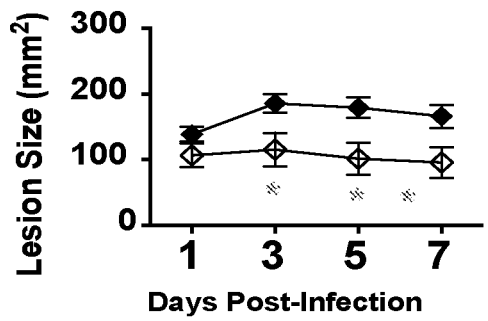
Figure 6B:
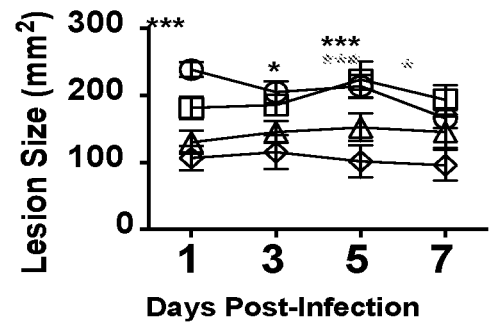
Figure 6C:
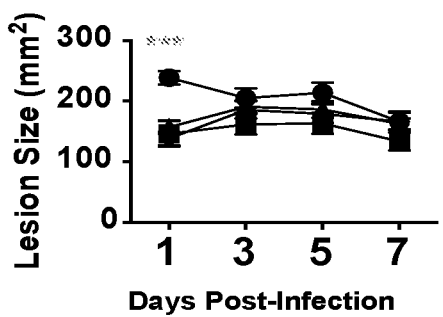

Next, we determined the in vivo relevance of primed macrophages in protection against recurring SSSI. BMDM from naïve or primed mice were recalled with either HKSA or LSA and then adoptively transferred into naïve recipient mice prior to MRSA SSSI challenge. Transfer of BMDM from primed mice recalled by in vitro pre-exposure to LSA, but not untreated or HKSA, significantly reduced abscess dermonecrosis area as compared to transfer of BMDM from naïve mice (FIG. 6A). In the primed group, only mice receiving BMDM recalled with LSA achieved reduced abscess severity as compared to controls receiving untreated BMDM (FIGS. 6B & 6C). Consistent with this outcome, only BMDM from primed mice recalled with LSA, but not HKSA, afforded reduced MRSA burden in abscesses compared to control (FIGS. 6D & 6E). Both naïve and primed BMDM recalled by exposure to either HKSA or LSA significantly reduced MRSA burden in kidney, as compared to mice that did not receive BMDM (FIGS. 6F & 6G). In contrast, neither naïve nor primed BMDM reduced the MRSA burden in the spleen (FIGS. 6H & 6I). Collectively, these data suggest that primary SSSI enhances protective immune memory by priming macrophages for enhanced staphylocidal activity in vivo.

Early Cytokine Responses (Day 2) Shape Protective Molecular and Cellular Responses Later in the Course of Infection (Day 7)

Analysis of cytokines of primed vs. naïve infections at days 2 and 7 revealed time-dependent responses in different tissues. These responses suggest different mechanisms of protection in localized vs. disseminated infection during recurrent MRSA SSSI. Hence, the current model afforded a unique opportunity to study mechanisms of protective host responses in context. In skin, priming results in early induction of IL-6 by day 2, followed by induction of IL-17A by day 7, which correlates with increased Th17 cell presence. IL-17A, produced by Th17 and other cells, has been shown to be protective in MRSA SSSI (see Chan L C, et al., 2015, Infection and immunity 83(11):4427-4437; Yeaman M R, et al., 2014, PNAS 111(51):E5555-5563; Miller L S & Cho J S, 2011, Nat Rev Immunol 11(8):505-518; Maher B M, et al., 2013, Infection and immunity 81(12):4478-4489; Montgomery C P, et al., 2014, Infection and immunity 82(5):2125-2134). Priming also resulted in increased DC populations in abscesses, which can produce IL-6 to mediate differentiation of Th17 cells (see Chen Y, et al., 2014, PloS one 9(3): e92450; Jung M Y, Son M H, Kim S H, Cho D, & Kim T S, 2011, Journal of immunology (Baltimore, Md.: 1950) 186 (12):6848-6859; Linehan J L, et al., 2015, PNAS 112(41): 12782-12787; Zheng T, et al., 2018, Science signaling 11(521)). Furthermore, priming resulted in increased expression of T cell chemokines MIG and RANTES in the skin, and IP-10 in the blood, ostensibly promoting T cell recruitment to abscesses (see Arai K, Liu Z X, Lane T, & Dennert G, 2002, Cellular immunology 219(1):48-56; Dufour J H, et al., 2002, Journal of immunology (Baltimore, Md.: 1950) 168(7):3195-3204; Eck M, et al., 2000, Clinical and experimental immunology 122(2):192-199; Groom J R & Luster A D, 2011, Experimental cell research 317(5):620-631; Lee J H, et al., 2017, Arthritis research & therapy 19(1):163; Liu M, et al., 2011, Cytokine & growth factor reviews 22(3): 121-130; Mikolajczyk T P, et al., 2016, FASEB journal 30(5):1987-1999; Tedla N, et al., 1996, The American journal of pathology 148(5):1367-1373). No changes in T cell populations were found in iLN, suggesting the expansion of Th17 cells occurs proximate to sites of infection. In contrast, priming resulted in decreased proportions of B cells relative to total CD45+ cells in the skin and draining iLN, suggesting a lesser role for humoral immunity during recurrent MRSA infection. Together, these results suggest that localized protective immune memory against recurring MRSA infection involves a robust and targeted Th17 response. In contrast, disseminated infection resulted in decreased IL-9 expression in the spleen, which is considered an autocrine cytokine for Th17 differentiation/expansion (Elyaman W, et al., 2009, PNAS 106(31):12885-12890). This finding suggests that Th9-mediated immunity is not significantly involved in protection during dissemination. Moreover, no changes in cell population or other cytokine levels were detected in the spleen.

Macrophages Contribute to Protection During Recurrent MRSA Infection

Priming resulted in increased M1 macrophage populations in the skin. In contrast to M2 macrophages, the M1 subtype is pro-inflammatory and involved in protection during MRSA infection (see Hanke M L, Heim C E, Angle A, Sanderson S D, & Kielian T, 2013, Journal of immunology (Baltimore, Md.: 1950) 190(5):2159-2168; Krysko O, et al., 2011, *Allergy* 66(3):396-403; Thurlow L R, et al., 2011, *Journal of immunology* (Baltimore, Md.: 1950) 186(11): 6585-6596). An increase in the total macrophage population, but not the proportion of M1 phenotype, was seen in the draining iLN. This finding is consistent with the concept that M1 macrophages in the skin undergo distinct polarization and functional differentiation from those in iLN. These data support the importance of IL-17A and M1 macrophages in localized protection during MRSA SSSI, as demonstrated by our prior studies and those of others (see Chan L C, et al., 2015, *Infection and immunity* 83(11):4427-4437; Yeaman M R, et al., 2014, *PNAS* 111(51):E5555-5563; Miller L S & Cho J S, 2011, *Nat Rev Immunol* 11(8):505-518; Maher B M, et al., 2013, *Infection and immunity* 81(12):4478-4489; Montgomery C P, et al., 2014, *Infection and immunity* 82(5):2125-2134). The finding that primed macrophages confer protective immunity to naïve mice affirmed these cells as capable of retaining anti-staphylococcal memory when recalled with *S. aureus*. This protection corresponded to greater intracellular killing of *S. aureus* specifically by primed macrophages in vitro. Remarkably, BMDM primed with *S. aureus* conferred protection against multiple strains of *S. aureus*, but did not enhance macrophage efficacy against other bacteria, suggesting specific macrophage memory.

Notably, BMDM underwent 14 days of differentiation in vitro prior to adoptive transfer and subsequent MRSA challenge, suggesting that their immune memory is durable. This concept was substantiated by the fact that only the adoptive transfer of primed BMDM recalled with LSA afforded protective immunity to naïve mice in skin during MRSA infection. These findings further imply that LSA boosts BMDM immune responses that are most relevant to localized efficacy in vivo, concordant with more robust stimulation of phagocytes by live vs. heat-killed organisms (see DeChatelet L R, Mullikin D, Shirley P S, & McCall C E, 1974, *Infection and immunity* 10(1):25-29).

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of preparing a population of target-primed macrophages, comprising culturing macrophages with a microorganism, in vitro or ex vivo, for 2 to 6 days under physiological conditions, thereby yielding the population of target-primed macrophages, wherein the macrophages have been prepared by isolating a monocyte or macrophage from a mammalian subject and differentiating or expanding the monocyte or macrophage, wherein the mammalian subject has been previously infected by or immunized with the microorganism, and wherein at least 50% of the target-primed macrophages in the population are M1-polarized macrophages.

2. The method of claim 1, wherein the microorganism is attenuated or inactivated.

3. The method of claim 2, wherein the inactivated microorganism is prepared as a cellular homogenate or whole-cell preparation.

4. The method of claim 1, wherein the M1-polarized macrophages have an immunophenotype signature of $CD38^+$ and $Egr2^-$.

5. The method of claim 4, wherein the M1-polarized macrophages further express the $CD45^+$, $CD11b^+$, $Ly6G^-$, and $F4/80^+$ phenotypes.

6. The method of claim 1, wherein no more than approximately 20% of the target-primed macrophages in the population are M2-polarized macrophages.

7. The method of claim 1, wherein the population of target-primed macrophages does not include B cell or T cell.

8. The method of claim 1, wherein the culturing is for a period from about 3 to 5 days, under physiological conditions.

9. The method of claim 1, wherein the microorganism comprises *S. aureus*.

10. The method of claim 1, further comprising administering the population of target-primed macrophages to a subject.

11. The method of claim 1, wherein the population of target-primed macrophages have organism-specific memory.

* * * * *